US006329178B1

(12) United States Patent
Patel et al.

(10) Patent No.: US 6,329,178 B1
(45) Date of Patent: Dec. 11, 2001

(54) DNA POLYMERASE MUTANT HAVING ONE OR MORE MUTATIONS IN THE ACTIVE SITE

(75) Inventors: Premal H. Patel; Lawrence A. Loeb, both of Bellevue, WA (US)

(73) Assignee: University of Washington, Seattle, WA (US)

(*) Notice: Subject to any disclaimer, the term of this patent is extended or adjusted under 35 U.S.C. 154(b) by 0 days.

(21) Appl. No.: 09/484,114

(22) Filed: Jan. 14, 2000

(51) Int. Cl.$^7$ .................................................. C12P 19/34
(52) U.S. Cl. ............................ 435/91.1; 435/5; 435/6; 435/91.2; 435/194; 435/320.1; 435/325; 435/419; 435/252.3; 536/23.2
(58) Field of Search ........................... 435/5, 6, 91.1, 435/91.2, 194, 320.1, 325, 419, 252.3; 536/23.2

(56) References Cited

U.S. PATENT DOCUMENTS

| | | |
|---|---|---|
| 4,683,202 | 7/1987 | Mullis . |
| 4,889,818 | 12/1989 | Gelfand et al. . |
| 5,939,292 | 8/1999 | Gelfand et al. . |
| 6,015,688 | * 1/2000 | Hughes et al. ........................ 435/6 |

FOREIGN PATENT DOCUMENTS

| | | |
|---|---|---|
| 0655 506 A1 | 5/1995 | (EP) . |
| 0 823 479 A2 | 11/1998 | (EP) . |
| 10-248583 | 9/1998 | (JP) . |
| WO 98/23733 | 6/1998 | (WO) . |
| WO 98/42873 | 10/1998 | (WO) . |
| WO 99/10366 | 3/1999 | (WO) . |

OTHER PUBLICATIONS

Fraser, C., et al., "Genomic sequence of a Lyme disease spirochaete, *Borrelia burgdorferi,* " Nature, 390:580–586 (1997).

Deckert, G. et al., Dna Polymerase I, *Nature*, 392:353–358 (1998) (abstract No. XP–002170186K).

Steiner, B.M., et al., "Sequencing and characterization of the Po1A gene from *Treponema pallidum*," *Science*, 281:375–388 (1988) (abstract No. XP–002170187).

Smith, H.O. and Venter, J.C., "Genomic sequence of a Lyme disease spirochaete, *Borrelia burgdorferi,*" *Nature*, 390:580–586 (1997) (Abstract No. XP–002170189).

Beese, L., et al., "Structure of DNA Polymerase I Klenow Fragment Bound to Duplex DNA," *Science* 260:352–355 (1993).

Boosalis, M., et al., "DNA Polymerase Insertion Fidelity," *J. Biol. Chem.* 262(30):14689–14696 (1987).

Desai and Pfaffle, "Single–step Purification of a Thermostabile DNA Polymerase Expressed in *Eschericia coli,*" *Biotechniques* 19:780–784 (1995).

Elena, S., et al., "Punctuated Evolution Caused by Selection of Rare Beneficial Mutations," *Science* 272:1802–4 (1996).

Engelke, D., et al., "Purification of *Thermus aquaticus* DNA Polymerase Expressed in *Escherichia coli,* "*Anal Biochem* 191: 396–400 (1990).

Fry and Loeb, *Animal Cell DNA Polymerases*, pp. 221, CRC Press, Inc., Boca Raton, FL. (1986).

Grimm and Arbuthnot, "Rapid purification of recombinant Taq DNA polymerase by freezing and high temperature thawing of bacterial expression cultures," *Nucleic Acids Res* 23:4518–9 (1995).

Innis, M., et al, Editors, *PCR Protocols*, San Diego, Academic Press, 1990, Ch 22, Entitled "Recombinant PCR," Higuchi, pp 177–183 (1990).

Kin and Loeb, "Human immunodeficiency virus reverse transcriptase substitutes for DNA polymerase I in *Escherichia coli,* " *Proc. Natl. Acad. Sci USA* 92:684–688 (1995).

Korberg and Baker, *DNA Replication*, pp. 929, W.H. Freeman and Co., New York (1992).

Kunkel, T., "DNA Replication Fidelity," *J. Biol. Chem.* 267(26):18251–18254 (1992).

LeClerc, J., et al., "High Mutation Frequencies Among *Escherichia coli* and *Salmonella* Pathogens," *Science* 274:1208–11 (1996).

Li, Y., et al., "Crystal structures of open and closed forms of binary and ternary complexes of the large fragment of *Thermus aquaticus* DNA polymerase I: structural basis for nucleotide incorporation," *Embo, J*. 17(24):7514–25 (1998).

(List continued on next page.)

*Primary Examiner*—Carla J. Myers
*Assistant Examiner*—Janell E. Taylor
(74) *Attorney, Agent, or Firm*—Albert P. Halluin; Viola T. Kung; Howrey, Simon, Arnold & White, LLP

(57) ABSTRACT

This invention provides a DNA polymerase that is a mutant form of a naturally occurring DNA polymerase, of which one or more amino acids in the active site are mutated. The DNA polymerase mutant of this invention is characterized by altered fidelity or altered enzymatic activity in comparison with the naturally occurring DNA polymerase. For example, the DNA polymerase mutant provides increased enzymatic activity, altered dNTP/rNTP specificity, or enhanced fidelity. In one aspect of the invention, the naturally occurring DNA polymerase comprises an amino acid sequence motif: AspTyrSerGlnIleGluLeuArg in the active site. In another aspect of the invention, the naturally occurring DNA polymerase comprises an amino acid sequence motif: LeuLeuValAlaLeuAspTyrSerGlnIleGluLeuArg in the active site. The mutant DNA polymerase has been altered in the active site of the naturally occurring DNA polymerase to contain either (a) two or more amino acid substitutions in the amino acid sequence motif, or (b) a substitution of an amino acid other than Glu in the amino acid sequence motif.

35 Claims, 4 Drawing Sheets

OTHER PUBLICATIONS

Loeb, L., "Transient Expression of a Mutator Phenotype in Cancer Cells," *Science* 277:1449–1450 (1997).

Mao, E., et al., "Proliferation of Mutators in A Cell Population," *J. Bacteriol.* 179(2):417–422 (1997).

Patel, P., et al., "Insights into DNA Polymerization Mechanisms from Structure and Function Analysis of HIV–1 Reverse Transcriptase," *Biochemistry* 34:5351–5363 (1995).

Sambrook, J., et al., *Molecular Cloning: A Laboratory Manual*, Cold Spring Harbor, Second Edition, Ch 15.51, "Oligonucleotide–Mediated Mutagenesis," (1989).

Sweasy and Loeb, "Mammalian DNA Polymerase β Can Substitute for DNA Polymerase I during DNA Replication in *Escherichia coli*," *J. Biol. Chem.* 267(3):1407–1410 (1992).

Tindall and Kunkel, "Fidelity of DNA Synthesis by the *Thermus aquaticus* DNA Polymerase," *Biochemistry* 27:6008–6013 (1988).

Wang, K., et al., "Crystal Structure of a pol α Family Replication DNA Polymerase from Bacteriophage RB69," *Cell* 89:1087–1099 (1997).

* cited by examiner

A

| | | | | | | | | | | | | |
|---|---|---|---|---|---|---|---|---|---|---|---|---|
| | | E | | | | | | | | | | C |
| | | F2 | | A4 | D12 | | | | | | | F |
| | | G | | E11 | E2 | | | | | | | G5 |
| | | H2 | F12 | F | G11 | | | C13 | | | | I2 |
| | | I21 | I | G3 | I | F2 | | D | | A | | K18 |
| | | K2 | M5 | I2 | K | I6 | | G10 | | K12 | | L |
| | | M | Q2 | K2 | N2 | M8 | | I | H17 | L7 | | M13 |
| | | P2 | R3 | L29 | P | P3 | | L | L15 | M18 | A | Q |
| | | Q8 | S3 | M21 | S6 | Q9 | | N20 | L15 | N2 | F10 | S15 |
| | | R8 | T | P | T14 | R | F12 | R30 | N | Q2 | I6 | T12 |
| | | T | V4 | S | V22 | S2 | H2 | T3 | R | T16 | P4 | V |
| | | V12 | W16 | T | Y3 | V21 | W | Y | S | V13 | V7 | W5 |
| T. aquaticus | | L | L | V | A | L | D | Y | S | Q | I | E | L | R |
| | | 605 | 606 | 607 | 608 | 609 | 610 | 611 | 612 | 613 | 614 | 615 | 616 | 617 |
| E. coli | | V | I | V | S | A | D | Y | S | Q | I | E | L | R |
| C. trachomatis | | Y | F | L | A | A | D | Y | S | Q | I | E | L | R |

B

| | | | | D2 | | | | | | | | |
|---|---|---|---|---|---|---|---|---|---|---|---|---|
| | E | F3 | | G2 | | | | | | | | |
| | H | I | A2 | K | F2 | | | C | | | | |
| | I8 | M2 | E6 | N | I | | | G6 | | K2 | | |
| | K | R | G2 | S | M3 | | | L | | M8 | | F |
| | Q4 | S | K | T1 | Q3 | | | N | | N | | K2 |
| | R8 | V3 | L9 | V2 | S | | | R9 | R | T3 | | M |
| | V3 | W2 | M8 | Y2 | V5 | F5 | | T2 | H4 | V5 | D8 | I2 | S |
| | L | L | V | A | L | D | Y | S | Q | I | E | L | R |

C

| | | | | | | | | | | | | |
|---|---|---|---|---|---|---|---|---|---|---|---|---|
| | | | L 1.0 | | | | | | | | | |
| | | | L 1.0 | | | | | G 1.1 | | | | |
| | | | L 1.0 | | | | | G 1.0 | | | | |
| | | | L 1.0 | | | | | R 0.8 | | | | F 2.0 |
| R 1.5 | | G 1.0 | | V 0.8 | | | | R 0.8 | | | | T 0.3 |
| R 1.2 | | A 1.0 | V 0.8 | V 0.5 | | | | C 0.6 | | | | M 0.3 |
| H 1.0 | | E 1.0 | V 0.8 | Q 0.7 | | | | C 0.5 | | M 1.2 | | M 0.2 |
| I 1.0 | R 1.0 | E 0.9 | V 0.8 | Q 0.6 | | | | C 0.4 | | M 1.0 | | M 0.1 |
| E 1.0 | F 0.9 | M 0.9 | T 0.4 | Q 0.5 | | | | C 0.4 | | K 0.7 | | Q 0.1 |
| V 0.7 | W 0.6 | M 0.6 | S 0.8 | M 0.5 | | F 0.8 | | N 0.2 | | T 0.4 | | G 0.1 |
| K 0.2 | W 0.5 | P 0.4 | D 0.2 | M 0.5 | | H 0.1 | | N 0.2 | | V 0.2 | | G 0.1 |
| L | L | V | A | L | D | Y | S | Q | I | E | L | R |

Figure 2 ial biology. Specifically, the present invention relates
DNA POLYMERASE MUTANT HAVING ONE OR MORE MUTATIONS IN THE ACTIVE SITE

FIELD OF THE INVENTION

The present invention relates generally to the field of molecular biology. Specifically, the present invention relates to a DNA polymerase that is a mutant form of a naturally occurring DNA polymerase, in which one or more amino acids within the active site are altered.

BACKGROUND OF THE INVENTION

DNA polymerases are responsible for the replication and maintenance of the genome, a role that is central to accurately transmitting genetic information from generation to generation. DNA polymerases function in cells as the enzymes responsible for the synthesis of DNA. They polymerize deoxyribonucleoside triphosphates in the presence of a metal activator, such as $Mg^{2+}$, in an order dictated by the DNA template or polynucleotide template that is copied. Even though the template dictates the order of nucleotide subunits that are linked together in the newly synthesized DNA, these enzymes also function to maintain the accuracy of this process. The contribution of DNA polymerases to the fidelity of DNA synthesis is mediated by two mechanisms. First, the geometry of the substrate binding site in DNA polymerases contributes to the selection of the complementary deoxynucleoside triphosphates. Mutations within the substrate binding site on the polymerase can alter the fidelity of DNA synthesis. Second, many DNA polymerases contain a proof-reading 3'-5' exonuclease that preferentially and immediately excises non-complementary deoxynucleoside triphosphates if they are added during the course of synthesis. As a result, these enzymes copy DNA in vitro with a fidelity varying from $5 \times 10_{-4}$ (1 error per 2000 bases) to $10^{-7}$ (1 error per $10^7$ bases) (Fry and Loeb, *Animal Cell DNA Polymerases*), pp. 221, CRC Press, Inc., Boca Raton, Fla. (1986); Kunkel, *J. Biol. Chem.* 267:18251–18254(1992)).

In vivo, DNA polymerases participate in a spectrum of DNA synthetic processes including DNA replication, DNA repair, recombination, and gene amplification (Korberg and Baker, *DNA Replication*, pp. 929, W. H. Freeman and Co., New York (1992)). During each DNA synthetic process, the DNA template is copied once or at most a few times to produce identical replicas. In vitro DNA replication, in contrast, can be repeated many times, for example, during polymerase chain reaction (Mullis, U.S. Pat. No. 4,683,202).

In the initial studies with polymerase chain reaction (PCR), the DNA polymerase was added at the start of each round of DNA replication (U.S. Pat. No. 4,683,202). Subsequently, it was determined that thermostable DNA polymerases could be obtained from bacteria that grow at elevated temperatures, and these enzymes need to be added only once (Gelfand, U.S. Pat. No. 4,889,818). At the elevated temperatures used during PCR, these enzymes would not denature. As a result, one can carry out repetitive cycles of polymerase chain reactions without adding fresh enzymes at the start of each synthetic addition process. DNA polymerases, particularly thermostable polymerases, are the key to a large number of techniques in recombinant DNA studies and in medical diagnosis of disease. For diagnostic applications in particular, a target nucleic acid sequence may be only a small portion of the DNA or RNA in question, so it may be difficult to detect the presence of a target nucleic acid sequence without PCR amplification. Due to the importance of DNA polymerases in biotechnology and medicine, it would be highly advantageous to generate DNA polymerase mutants having desired enzymatic properties such as altered fidelity and high activity.

Polymerases contain an active site architecture that specifically configures to an incorporates each of the four deoxynucleoside triphosphates while taking direction from templates with diverse nucleotide sequences. In addition, the active site tends to exclude altered nucleotides produced during cellular metabolism. The overall folding pattern of polymerases resembles the human right hand and contains three distinct subdomains of palm, fingers and thumb. (Beese et al., *Science* 260:352–355 (1993); Patel et al., *Biochemistry* 34:5351–5363 (1995); these two references are incorporated herein by reference. While the structure of the fingers and thumb subdomains vary greatly between polymerases that differ in size and in cellular functions, the catalytic palm subdomains are all superimposable. Motif A, which interacts with the incoming dNTP and stabilizes the transition state during chemical catalysis, is superimposable with a mean deviation of about one Å amongst mammalian pol α and prokaryotic pol I family DNA polymerases (Wang, et al., *Cell* 89:1087–1099 (1997)). Motif A begins structurally at an antiparallel β-strand containing predominantly hydrophobic residues and continues to an α-helix (FIG. 1). The primary amino acid sequence of DNA polymerase active sites are exceptionally conserved. Motif A retains the sequence DYSQIELR in polymerases from organisms separated by many millions years of evolution including *Thermus aquaticus*, *Chlamydia trachomatis*, and *Escherichia coli*. Taken together, these results indicate polymerases function by similar catalytic mechanisms and that the active site of polymerases may be immutable in order to ensure the survival of organisms.

U.S. Pat. No. 5,939,292 is directed to a recombinant thermostable DNA polymerase that is a mutant form of a naturally occurring thermostable DNA polymerase, wherein said naturally occurring thermostable DNA polymerase has an amino acid sequence comprising amino acid sequence motif SerGlnIleGluLeuArgXaa (SEQ ID NO:1) wherein "Xaa" at position 7 of said sequence motif is a valine residue or an isoleucine residue; wherein said mutant form has been modified to contain an amino acid other than glutamic acid (Glu) at position 4 of said sequence motif; and wherein said mutant form possesses reduced discrimination against incorporation of an unconventional nucleotide in comparison to said naturally occurring thermostable DNA polymerase. In the '292 patent, the thermostable DNA polymerase mutant has an activity to incorporate ribonucleotides in vitro. The mutant has a single mutation in the active site, namely, the glutamic acid residue is altered. We believe that bacteria dependent on such a DNA polymerase mutant with a single mutation of altering glutamic acid residue in the active site is not able to survive in vivo because the mutant does not have enough activity for DNA replication. Our results suggest that bacteria depending on a DNA polymerase mutant which has a Glu615 residue substitution will only survive if the Glu is substituted by Asp and there is at least one additional substitution at other sites in motif A (FIG. 2).

The present invention evaluates the degree of mutability of a polymerase active site in vivo. Our results counter the common paradigm that amino acid substitutions within the catalytic site lead to reduced stability and enzymatic activity. We find that the DNA polymerase active site is highly mutable and can accommodate many amino acid substitutions without affecting DNA polymerase activity significantly. The instant application shows that mutation on the catalytic site can produce highly active enzymes with altered substrate specificity. Mutant DNA polymerases may offer selective advantages such as ability to resist incorporation of chain terminating nucleotide analogs, increased catalytic activity, ability to copy through hairpin structures, increased processivity, and altered fidelity.

SUMMARY OF THE INVENTION

This invention is directed to a DNA polymerase that is a mutant form of a naturally occurring DNA polymerase, in which one or more amino acids in the active site is mutated. The DNA polymerase mutant of this invention is characterized by altered substrate specificity, altered fidelity or higher enzymatic activity in comparison with the naturally occurring DNA polymerase. A host cell dependent on the DNA polymerase mutant is able to survive and replicate repetitively. The invention also provides a method of preparing a recombinant DNA polymerase that is a mutant form of a naturally occurring DNA polymerase, in which one or more amino acids in the catalytic site is mutated.

In one aspect of the invention, the naturally occurring DNA polymerase comprises an amino acid sequence motif AspTyrSerGlnIleGluLeuArg (SEQ ID NO: 2) in the active site. The mutant form has been altered to contain either (a) two or more amino acid substitutions in that amino acid sequence motif, or (b) one amino acid substitution that is not Glu in that amino acid sequence motif.

In another aspect of the invention, the naturally occurring DNA polymerase comprises an amino acid sequence motif: LeuLeuValAlaLeuAspTyrSerGlnIle GluLeuArg (SEQ ID NO: 3) in the active site. The mutant form has been altered to contain either (a) two or more amino acid substitutions in that amino acid sequence motif, or (b) one amino acid substitution that is not Glu in that amino acid sequence motif.

The present invention discovers that the active site of a polymerase is highly mutable and can accommodate many amino acid substitutions without affecting DNA polymerase activity. Substitutions of amino acids within Motif A of a DNA polymerase produce enzymes with altered catalytic activity, with altered dNTP/rNTP specificity, with low fidelity that is capable of incorporating unconventional nucleotides, and with high fidelity that is suitable for a polymerase chain reaction. For example, the mutant DNA polymerases are characterized by the ability to more efficiently incorporate unconventional nucleotides, particularly ribonucleotides and their analogs, than the corresponding wild-type enzymes.

BRIEF DESCRIPTION OF THE FIGURES

FIG. 2 demonstrates high mutability of Motif A. The sequence of Motif A ($D^{610}YSQIELR^{617}$, (SEQ ID NO: 2)) has been retained after evolution through many millions of years in organisms such as Thermus aquaticus (SEQ ID NO: 3), Escherichia coli (SEQ ID NO: 4), and Chlamydia trachomatis (SEQ ID NO: 5). To test the importance of this conservation, residues L605 to R617 were randomly mutated such that each contiguous amino acid can be replaced by potentially any of the other 19. (A) The degree of mutability of each amino acid within Motif A from all active clones (>10% to 200% activity relative to wild type (WT)) complimenting an E. coli DNA polymerase I temperature sensitive strain. Amino acid substitutions at the locus are listed, along with the number of times each substitution is observed. (B) Mutations in clones exhibiting high activity (66% to 200% WT). (C) Mutations in clones containing a single amino acid substitution followed by activity relative to WT.

DETAILED DESCRIPTION OF THE INVENTION

Figure 1:
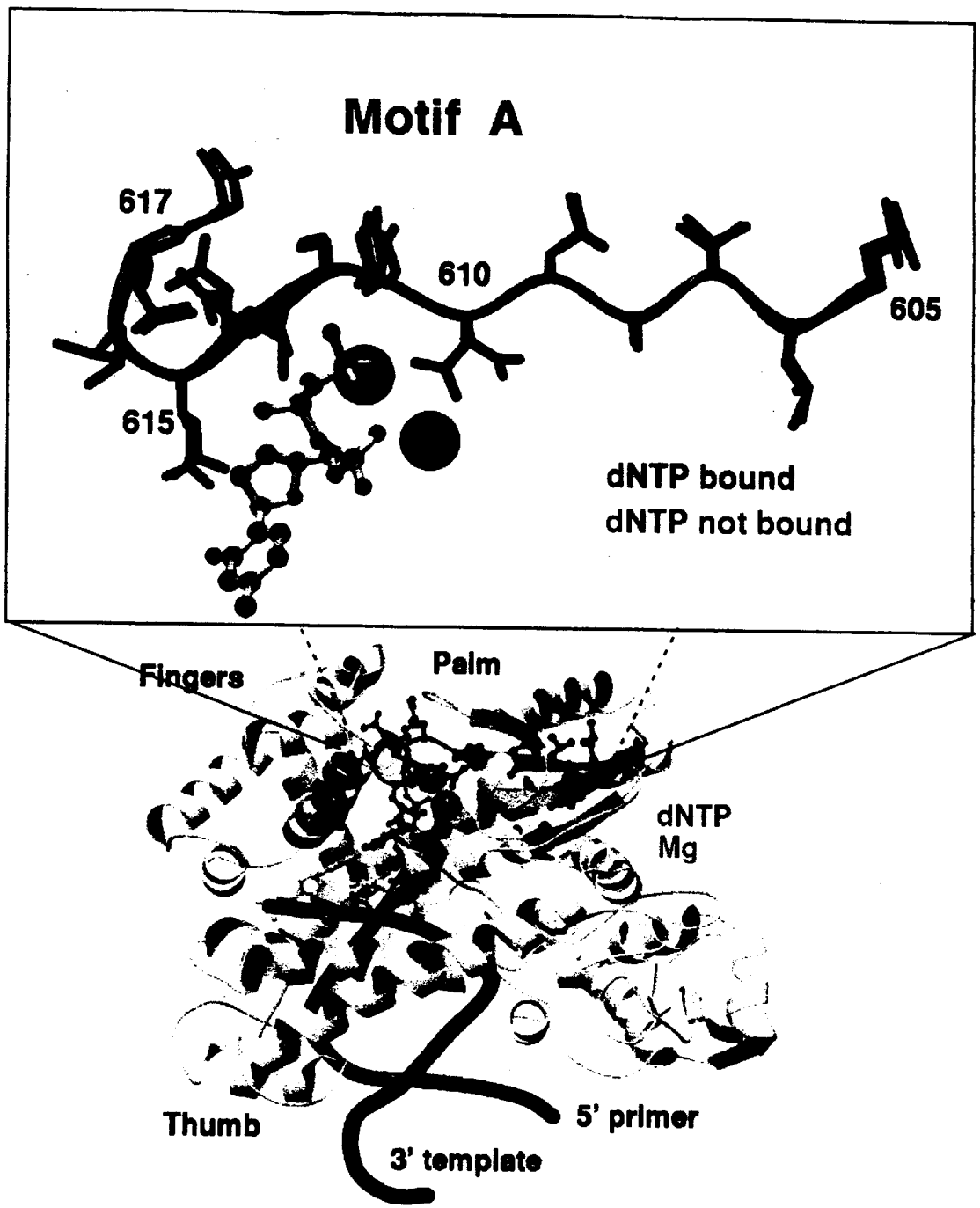
FIG. 1 depicts Structure of Taq pol I bound with DNA and incoming dNTP. Evolutionarily conserved Motif A (amino acids 605 to 617 highlighted in red) is located within the heart of the polymerase catalytic site. Residues of Motif A interact with the incoming dNTP and amino acids in the finger motif during the conformational change step, subsequent to nucleotide binding. Motif A is superimposable in all polymerases with solved structures and begins at a hydrophobic anti parallel β sheet that proceeds to an α helix. The orientation of side chains within amino acids of Motif A is nearly identical prior (in blue) and subsequent (in red) to dNTP binding, with the exception of Asp610, which rotates around the β carbon while coordinating with the $Mg^{+2}$-dNTP complex. Coordinate sets 2ktq (Taq pol I, ternary complex, open form), 3ktq (ternary complex, closed form), and 4ktq (binary complex) were obtained from Protein Data Bank.

The present invention provides a novel composition of a DNA polymerase that is a mutant form of a naturally occurring DNA polymerase, in which one or more amino acids in the catalytic site is mutated. The mutant DNA polymerases of this invention are active enzymes with same or altered substrate specificity. They are characterized in altered catalytic activity and/or altered fidelity. The low fidelity mutants are useful for introducing mutations into specific genes due to the increased frequency of misincorporation of nucleotides during an error-prone PCR application. The high fidelity mutants are useful for PCR amplification of genes and for mapping of genetic mutations. The mutants are therefore useful for the characterization of specific genes and for the identification and diagnosis of human genetic diseases.

To facilitate understanding of the invention, a number of terms are defined below. The term "mutant DNA polymerase" is intended to refer to a DNA polymerase that contains one or more amino acids in the active site that differ from a selected naturally occurring DNA polymerase such as that within the Pol I family of DNA polymerases. The selected DNA polymerase is determined based on desired enzymatic properties and is used as a parent polymerase to generate a population of mutant polymerases. For example, a thermostable polymerase such as Taq DNA polymerase I or a E. coli DNA polymerase I can be selected, for example, as a naturally occurring DNA polymerase to generate a population of DNA polymerase mutants. The "mutant DNA polymerase" of this invention is not limited to a mutant produced by recombinant techniques; the mutant can be produced by other methods, for example, chemical or radiation mutagenesis.

The term "catalytic activity" or "activity" when used in reference to a DNA polymerase is intended to refer to the enzymatic properties of the polymerase. The catalytic activity includes, for example: enzymatic properties such as the rate of synthesis of nucleic acid polymers; the $K_m$ for substrates such as nucleoside triphosphates and template strand; the fidelity of template-directed incorporation of nucleotides, where the frequency of incorporation of non-complementary nucleotides is compared to that of complementary nucleotides; processivity, the number of nucleotides synthesized by a polymerase prior to dissociation from the DNA template; discrimination of the ribose sugar; and stability, for example, at elevated temperatures. DNA polymerases also discriminate between deoxyribonucleoside triphosphates and dideoxyrobonucleoside triphosphates. Any of these distinct enzymatic properties can be included in the meaning of the term catalytic activity, including any single property, any combination of properties or all of the properties. The present invention includes polymerase mutants having altered catalytic activity distinct from altered fidelity.

The term "fidelity" when used in reference to a DNA polymerase is intended to refer to the accuracy of template-directed incorporation of complementary bases in a synthesized DNA strand relative to the template strand. Fidelity is measured based on the frequency of incorporation of incorrect bases in the newly synthesized nucleic acid strand. The incorporation of incorrect bases can result in point mutations, insertions or deletions. Fidelity can be calculated according to the procedures described in Tindall and Kunkel (*Biochemistry* 27:6008–6013 (1988)).

The term "altered fidelity" refers to the fidelity of a mutant DNA polymerase that differs from the fidelity of the selected parent DNA polymerase from which the DNA polymerase mutant is derived. The altered fidelity can either be higher or lower than the fidelity of the selected parent polymerase. Thus, DNA polymerase mutants with altered fidelity can be classified as high fidelity DNA polymerases or low fidelity DNA polymerases. The term "high fidelity" is intended to mean a frequency of accurate base incorporation that exceeds a predetermined value. Similarly, the term "low fidelity" is intended to mean a frequency of accurate base incorporation that is lower than a predetermined value. The predetermined value can be, for example, a desired frequency of accurate base incorporation of the fidelity of a wild type DNA polymerase. Altered fidelity can be determined by assaying the parent and mutant polymerase and comparing their activities using any assay that measures the accuracy of template directed incorporation of complementary bases. Such methods for measuring fidelity include, for example, a primer extension assay, as well as other methods known to those skilled in the art.

The term "conventional" when referring to nucleic acid bases, nucleoside, or nucleotides refers to those which occur naturally in the polynucleotide being described (i.e., for DNA these are dATP, dGTP, dCTP and dTTP). Additionally, c7dGTP and dITP are frequently utilized in place of dGTP (although incorporated with lower efficiency) in in vitro DNA synthesis reactions, such as sequencing. Collectively, these may be referred to as dNTPs.

The term "unconventional" when referring to a nucleic acid base, nucleoside, or nucleotide, includes modification, derivations, or analogues of conventional bases, nucleosides, or nucleotides that naturally occur in DNA or RNA. More particularly, as used herein, unconventional nucleotides are modified at the 2' position of the ribose sugar in comparison to conventional dNTPs. Thus, although for RNA the naturally occurring nucleotides are ribonucleotides (i.e., ATP, GTP, CTP, UTP collectively rNTPs), because these nucleotides have a hydroxyl group at the 2' position of the sugar, which, by comparison is absent in dNTPs, as used herein, ribonucleotides are unconventional nucleotides as substrates for DNA polymerases. Ribonucleotide analogues containing substitutions at the 2' position, such as 2'-fluoro or 2'-amino, are within the scope of the invention. Additionally, ribonucleotide analogues may be modified at the 3' position, for example, wherein the normal hydroxyl is replaced with a hydrogen (3' deoxy), providing a ribonucleotide analogue terminator. Such nucleotides all are included within the scope of the term "unconventional nucleotides."

Unconventional bases may be bases labeled with a reporter molecule such as a fluorophore, a hapten, a radioactive molecule or a chemiluminescent molecule. For example, bases may be fluorescently labeled with fluorescein, or rhodamine; hapten- labeled with biotin or digioxigenin; or isotopically labeled.

The term "expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may also be integrated into the host chromosome.

The term "gene" refers to a DNA sequence that comprises control and coding sequences necessary for the production of a recoverable bioactive polypeptide or precursor. The polypeptide can be encoded by a full-length gene sequence or by any portion of the coding sequence so long as the enzymatic activity is retained.

The term "host cell(s)" refers to both single cellular prokaryote and eukaryote organisms such as bacteria, yeast, and actinomycetes and single cells from higher order plants or animals when being grown in cell culture.

The mutant DNA polymerases of this invention comprises a mutation in the active site; the mutation is either a single amino acid substitution or multiple amino acid substitutions. The structures of active sites are superimposable among different naturally occurring DNA polymerases. Motif A, the active site of a DNA polymerase, which interacts with the incoming dNTP and stabilizes the transition state during chemical catalysis, is superimposable with a mean deviation of about one Å amongst mammalian pol I and prokaryotic pol I family DNA polymerases. The sequence of DYSQIELR in motif A is conserved among procaryotic organisms such as *Thermus aquaticus, Chlamydia trachomatis*, and *Escherichia coli*. Table 1 lists the amino acid sequences of motif A of different organisms. Of the 34 species listed, 27 comprise DYSQIELR (SEQ. ID NO: 2) in motif A, the remaining have an amino acid sequence of DYSQIEMR (SEQ. ID NO: 6), DFSQIELR (SEQ. ID NO: 7), DYSQIELA (SEQ. ID NO: 8), DYVQIELR (SEQ. ID NO: 9) or DYTQIELY (SEQ. ID NO: 10); none of the species have E altered in motif A. The mutant DNA polymerases of this invention comprises a mutation in an active site of a naturally occurring DNA polymerase which comprises an amino acid sequence of DYSQIELR, DYSQIEMR, DFSQIELR, DYSQIELA, DYVQIELR or DYTQIELY. In one preferred embodiment of the invention, the critical motif of a naturally occurring DNA polymerase to be modified comprises an amino acid sequence DYSQIELR (AspTyrSerGlnIleGluLeuArg). In another preferred embodiment, the critical motif to be modified comprises an amino acid sequence LLVALDYSQIELR (LeuLeuVal AlaLeuAspTyrSerGlnIleGluLeuArg), an amino acid sequence in motif A of Taq Pol I. The present invention also provides an isolated nucleic acid sequence encoding a DNA polymerase mutant as described above.

TABLE 1

| Organism | Motif A sequence |
| --- | --- |
| Thermus aquaticus | DYSQIELR |
| Thermus thermophilus | DYSQIELR |
| Thermus caldophilus | DYSQIELR |
| Thermus flavus | DYSQIELR |
| Thermus filiformis | DYSQIELR |
| Escherichia coli (K12) | DYSQIELR |
| Mycobacterium tuberculosis | DYSQIEMR |
| Mycobacterium smegmatis | DYSQIEMR |
| Mycobacterium leprae | DYSQIEMR |
| Rickettsia felis | DYSQIELR |
| Rickettsia helvetica | DYSQIELR |
| Rickettsia rhipicephali | DYSQIELR |
| Rickettsia montanensis | DYSQIELR |
| Rickettsia sibirica | DYSQIELR |
| Rickettsia rickettsii (84-21C) | DYSQIELR |
| Rickettsia typhi | DYSQIELR |
| Rickettsia prowazekii (B) | DYSQIELR |
| Rickettsia prowazekii (Madrid) | DYSQIELR |
| Bacillus subtilis | DYSQIELR |
| Bacillus stearothermophilus | DYSQIELR |
| Chlamydia trachomatis | DYSQIELR |
| Chlamydophila pneumoniae | DYSQIELR |
| Chloroflexus aurantiacus | DYSQIELR |
| Haemophilus influenzae | DYSQIELR |
| Helicobacter pylori | DYSQIELR |
| Lactococcus lactis | DYSQIELR |
| Methylobacterium | DYSQIELR |
| Streptococcus pneumoniae | DYSQIELR |
| Streptomyces coelicolor | DYSQIELR |
| Synechocystis sp. (PCC6803 II) | DYSQIELR |
| Aquifex aeolicus | DFSQIELR |
| Borrelia burgdorferi | DYSQIELA |
| Rhodothermus obamensis | DYVQIELR |
| Treponema pallidum | DYTQIELV |

By random mutagenesis protocol, a large population of mutants in which each amino acid is altered to potentially any of the other nineteen amino acids are created. When coupled with a stringent selection scheme, the nature of allowable amino acid substitutions in vivo can be determined after sequencing selected mutants. The mutations in motif A of an active mutant DNA polymerase include only conservative substitutions at sites that stabilize the tertiary structure, but include a wide variety of amino acid substitutions at other sites. All the mutants selected in this invention have at least 10% of WT DNA polymerase activity. Host cells that depend on the mutant DNA polymerases are able to live and replicate repetitively. After selection, plasmids containing genes that encoding active DNA polymerase mutants are purified, and nucleic acid sequences encoding the mutant DNA polymerases are determined by sequence analysis. The amino acid sequences of motif A of the mutants are derived from the nucleic acid sequences. The unique properties exhibited by the DNA polymerase mutants include DNA polymerase activity higher than the wild type (WT) enzyme, the ability to incorporate unconventional nucleotides such as ribonucleotides, analogs of ribonucleotides, and bases labeled with fluorescent of hapten tags. A preferred DNA polymerase mutant of this invention is characterized by its ability to incorporate ribonucleotides at a rate of at least 10-fold, preferably 100-fold, and more preferably 1000-fold, greater than that of WT DNA polymerase, and/or the ability to function as both DNA and RNA polymerases.

Sequence analysis of active mutant DNA polymerases, for example, mutants of Taq Pol I, shows that some Motif A residues tolerate a wide spectrum of substitutions (Ser612Ile614, and Arg617), some residues tolerate conservative substitutions (Tyr611, Gln613, Glu615, and Leu 616), and only one residue is immutable (Asp610). Of the highly mutable residues, Ser612, which is present in nearly all eukaryotic and prokaryotic DNA polymerases studied, tolerates substitutions that are diverse in size and hydrophilicity while often preserving WT-like activity. Of the other highly mutable amino acids, hydrophobic residues Leu605 to Leu609 form a strand of the structurally conserved anti-parallel β sheet that accommodates the triphosphate portion of the incoming dNTP. Presumably those residues that tolerate conservative changes (Tyr611, Gln613, Glu615, and Leu616) are important for dNTP binding and/or protein stability; X-ray structure analysis show that each of these residues has a potential role in protein interactions with important domains (Li, Embo, J. 17:7514–25 (1998)). Three residues (Gln613, Glu615, and Leu616) are involved in interactions with the fingers motif O helix as it changes conformation during the dNTP binding step and the forth (Tyr611) serves as an important anchor as well as providing a carboxyl oxygen that binds one of the metals. The only immutable residue is Asp610, which even in the context of other mutations can not be substituted even by glutamic acid. Asp610 functions to coordinate the metal-mediated catalysis reaction, leading to the incorporation of the incoming nucleotide. The immutable nature of Asp610 indicates the geometry of the active site at this precise catalytic locus can not be altered. The analysis of mutants with a single amino acid allows the determination of the effect on activity conferred by specific amino acid substitutions. Leu605Arg confers greater polymerase activity relative to WT Taq pol I, and all selected Leu605Arg mutants occurring in context of multiple mutations also exhibit high activity. The single substitution, Arg617Phe, confers twice the activity of WT Taq Pol I, while other substitutions at this locus lower Taq pol I activity.

A subset of mutants in our library incorporate rNTPs efficiently (Table 2). The present invention provides compositions of mutant DNA polymerases which comprise an amino acid sequence as listed in Table 2 in the active site (SEQ ID NOs: 11–33). Preferred compositions of mutant DNA polymerases comprise an amino acid sequence of LLVSLDYSQNELR (SEQ ID NO: 14), LLVALDYSQNEIR (SEQ ID NO: 21) or LLVDLDYSQIDLR (SEQ ID NO: 24) in the active site. The mutants of Table 2 contain 1, 2, 3 and 4 amino acid substitutions and fall into two major classes: 1) Those encoding a hydrophilic substitution at Ile614; these enzymes constitute the majority of rNTP incorporating mutants with 1 or 2 substitutions, and 2) those that encode a Glu615Asp substitution; these enzymes contain 1–3 other substitutions and have a total of 2–4 substitutions. None of our mutants contain a single Glu615 substitution. Our results suggest that Glu615 is important for dNTP binding and DNA polymerase activity. A single mutation in motif A which alters the glutamic acid may fatally impair the DNA polymerase activity. A conservative substitution of Glu to Asp plus additional compensating mutations in motif A may provide a proper tertiary structure for the DNA polynerase activity. Kinetic analysis shows purified WT Taq pol I does not efficiently incorporate ribonucleotides. Our DNA polymerase mutants incorporate each ribonucleotide up to three orders of magnitude more efficiently than the WT polymerase.

TABLE 2

Sequences of rNTP incorporating Taq polymerases

| #aa subs | Mutant | L | L | V | A | L | D | Y | S | Q | 614 I | 615 E | L | 617 R |
|---|---|---|---|---|---|---|---|---|---|---|---|---|---|---|
| 1 | 53† |   |   |   |   |   |   |   |   |   |   | K |   |   |
|   | 75 |   |   |   |   |   |   |   |   |   |   | M |   |   |
|   | 65 |   |   |   | D |   |   |   |   |   |   |   |   | P |
|   | 94 |   |   |   | S |   |   |   |   |   |   | N |   |   |
|   | 164 | V |   |   |   |   |   |   |   |   |   | K |   |   |
|   | 187 |   |   |   |   |   |   |   |   | L |   | K |   |   |
|   | 198 |   |   |   |   |   |   | M |   |   |   | Q |   |   |
|   | 205 |   |   |   |   |   |   |   |   | L |   | Q |   |   |
|   | 221 |   | V |   |   |   |   |   |   |   |   | D |   |   |
|   | 230 |   |   |   |   |   |   |   |   | R |   |   | F |   |
|   | 265 |   |   |   |   |   |   |   |   |   |   | N | I |   |
|   | 273 |   |   |   |   | G |   |   |   |   |   | D |   |   |
|   | 340 |   |   |   |   | V |   |   |   |   |   | D |   |   |
|   | 346 |   |   |   |   | D |   |   |   |   |   | D |   |   |
| 3 | 79 |   |   |   |   | D | V |   |   |   |   | D |   |   |
|   | 159 | I |   | L |   |   |   |   |   |   |   | K |   |   |
|   | 166 |   |   | M |   |   |   |   |   |   |   | M | D |   |
|   | 175‡ |   |   |   |   |   |   |   | F |   |   | T | D |   |
|   | 298 |   |   |   |   | V | V |   |   |   |   | K |   |   |
|   | 299 |   |   |   |   |   |   |   |   |   |   | T | F | W |
|   | 300‡ |   |   |   |   |   |   |   | F |   |   | T | D |   |
| 4 | 26 |   |   | M | V | V |   |   |   |   |   | D |   |   |
|   | 48 |   |   |   |   |   |   |   | R |   |   | K | D | M |

†underline denotes mutants exhibit wt activity
‡these two mutants differ in nucleotide sequence We propose two mechanisms by which the steric interference conferred by Glu615 on an incoming ribonucleotide (FIG. 1) can be alleviated while still allowing utilization of dNTPs. 1) Hydrophilic substitutions at Ile614 could alter the steric environment by interacting with and repositioning the adjacent Glu615. 2) The Glu615Asp substitution reduces the length of the side chain and diminishes blockage while still allowing the essential hydrogen bonding to the helix O residue Tyr671.

To determine if the polymerases mutant can function as RNA polymerases by incorporating multiple ribonucleotides sequentially, the purified WT Taq pol I, a mutant containing substitution at I614, and a mutant containing a substitution at E615, are incubated with increasing amounts of all four rNTPs. While the WT enzyme inefficiently incorporates and extends ribonucleotides, both classes of rNTP utilizing mutant enzymes polymerize multiple ribonucleotides, even at rNTP concentrations well below that found in cells. In control incubations the elongated products can be degraded in alkali to regenerate the initial substrate, illustrating the products are RNA. Thus, our random mutagenesis protocol has identified a set of DNA polymerases containing 1–2 gain of function mutations conferring the ability to incorporate successive ribonucleotides. Even though these mutants may confer a reduced fitness to the cells over long term by incorporating ribonucleotides into chromosomal DNA, the observation that 23 independent rNTP incorporating mutants are selected using a DNA polymerase-deficient strain indicates that a functioning DNA polymerase is important for survival, even if this polymerase transiently incorporates ribonucleotides during the first >50 generations.

The present invention provides mutant DNA polymerases suitable for use with ribonucleoside triphosphates for numerous applications including nucleic acid amplification, nucleic acid detection and DNA sequencing analysis. The use of ribonucleotides in sequencing avoids the high cost of chain-terminating analogues, such as ddNTPs. In addition, it facilities the preparation of novel amplification products suitable not only for DNA sequence analysis but also for other types of analysis such as electrophoresis or hybridization without the need to conduct subsequent DNA sequencing reactions.

The present invention provides a mutant DNA polymerase that can incorporate a reporter-labeled nucleotide analog, for use in diagnosis of disease. In this application, DNAs from specific pathogens such as bacteria or viruses can be detected from a clinical sample (e.g., blood, urine, sputum, stool, sweat, etc.) The sample is first heated to expose its genome and to denature its DNAs. Next, a small single-stranded DNA fragment that is complementary to a region of the pathogen's genome is added such that the DNA fragment can hybridize with a complementary region of the pathogen's genomic DNAs. Then, a mutant DNA polymerase of the present invention that can efficiently incorporate a reporter-labeled nucleotide analog is added in the presence of all four dNTPS and a trace amount of a reporter-labeled nucleotide analog. The reporter molecule can be a fluorophore such as fluorescein, Texas red, rhodamine, Cascade Blue dye, etc., a hapten such as biotin or digioxigenin, a radiolabel, or a chemiluminescent molecule. Extension of the small-hybridized DNA fragment by the mutant DNA polymnerase results in a "tagged" DNA fragment. The presence of an abundant amount of tagged DNAs signifies the presence of a specific pathogen. This protocol can be modified by fluorescently labeling many different sets of small single-stranded DNA; each contains a different fluorophore and exhibits a different emission spectrum (e.g., red, blue, magenta, yellow, etc.) Each small single-stranded DNA can hybridize to the genome of one of the many distinct pathogenic agents. Following DNA synthesis by a mutant polymerase in the presence of a uniquely fluorescently labeled nucleotide, a specific pathogen can be diagnosed by determining the nature of the fluorescent signal from the extended DNAs.

The present invention provides a mutant DNA polymerase that has a higher fidelity comparing with a WT DNA polymerase. The mutant DNA polymerase are useful in copying or repetitive DNA sequences, for the application in cancer diagnostics, and in gene therapy/cancer therapy to kill tumors via incorporation of toxic analogs.

The present invention also provides mutant DNA polymerases having enhanced fidelity compared with WT DNA polymerase. For example, one mutant with six substitutions (Leu605Arg, Leu606Met, Val607Lys, Ala608Ser, Leu609Ile and Ser612Arg) exhibits about 5-fold higher fidelity than the WT Taq Pol I. The invention provides a method of using high fidelity DNA polymerase mutants, which comprise a mutation in the active site, for amplifying a specific nucleic acid sequence in a polymerase chain reaction,. The polymerase chain reaction is described in detail in U.S. Pat. No. 4,683,202; the reference is incorporated herein by reference. Briefly, the specific nucleic acid sequence consists of two separate complementary strands and is contained in a nucleic acid or a mixture of nucleic acids. The amplification method comprises the steps of: (a) treating the two strands with two oligonucleotide primers in the presence of a high fidelity mutant DNA polymerase, under conditions such that an extension product of each primer is synthesized which is complementary to each nucleic acid strand of the specific nucleic acid sequence, wherein said primers are selected so as to be sufficiently complementary to the two strands of the specific sequence to hybridize therewith, such that the extension product synthesized from one primer, when it is separated from its complement, can serve as a template for synthesis of the extension product of the other primer; (b) separating the primer extension products from the templates on which they were synthesized to produce single-stranded molecules; and (c) treating the single-stranted molecules generated from step (b) with the primers of step (a) in the presence of the mutant DNA polymerase, under conditions that a primer extension product is synthesized using each of the single strands produced in step (b) as a template. In a preferred method, step (b) is accomplished by denaturing such as heating. One of the DNA polymerase mutants suitable for the PCR application comprises an amino acid sequence of RMKSIDYRQIELR (SEQ ID NO: 34).

A mutant DNA polymerase of the present invention have a molecular weight in the range of 85,000 to 105,000, more preferably between 90,000 to 95,000. The amino acid sequence of these polymerases consists of about 750 to 950 amino acid residues, preferable between 800 and 900 amino acid residues. The polymerases of the present invention may also consist of about 540 or more amino acids and comprise at least the polymerase domain, and a portion corresponding to the 3' to 5' exonuclease domain and possibly parts of the 5' to 3' exonuclease domain, which is contained on the first one-third of the amino acid sequence of many full-length thermostable polymerase enzymes.

Exemplary mutant DNA polymerases of the present invention are recombinant derivatives of the native polymerases from the organisms listed in Table 1. Table 1 also indicates the particular sequence of the critical motif in which a mutation occurs. For DNA polymerases not shown in Table 1, preparing a mutant polymerase is simple once the critical motif in the amino acid sequence is identified.

The invention provides a method for identifying a mutant DNA polymerase having altered fidelity or catalyic activity. The method consists of generating a random population of polymerase mutants by mutating at least one amino acid residue in motif A of a naturally occurring DNA polymerase and screening the population for active polymerase mutants by genetic selection.

The generation and identification of polymerases having altered fidelity or altered catalytic activity is accomplished by first creating a population of mutant polymerases comprising randomized oligonucleotides within motif A. The identification of active mutants is performed in vivo and is based on genetic complementation of conditional polymerase mutants under non-permissive conditions. Once identified, the active polymerases are then screened for fidelity of polynucleotide synthesis and for catalytic activity.

The methods of the invention employ a population of polymerase mutants and the screening of the polymerase mutant population to identify an active polymerase mutant. Using a population of polymerase mutants is advantageous in that a number of amino acid substitutions including a single amino acid substitution and multiple amino acid substitutions can be examined for their effect on polymerase fidelity. The use of a population of polymerase mutants increases the probability of identifying a polymerase mutant having a desired fidelity.

Screening a population of polymerase mutants has the additional advantage of alleviating the need to make predictions about the effect of specific amino acid substitutions on the activity of the polymerase. The substitution of single amino acids has limited predictability as to its effect on enzymatic activity and the effect of multiple amino acid substitutions is virtually unpredictable. The methods of the invention allow for screening a large number of polymerase mutants which can include single amino acid substitutions and multiple amino acid substitutions. In addition, using screening methods that select for active polymerase mutants has the additional advantage of eliminating inactive mutants that could complicate screening procedures that require purification of polymerase mutants to determine activity.

Moreover, the methods of the invention allow for targeting of amino acid residues adjacent to immutable or nearly immutable amino acid residues. Immutable or nearly immutable amino acid residues are residues required for activity, and those immutable residues located in the active site provide critical residues adjacent to these required residues provides the greatest likelihood of modulating the activity of the polymerase. Introducing random mutations at these sites increases the probability of identifying a mutant polymerase having a desired alteration in activity such as altered fidelity.

A naturally occurring DNA polymerase is selected as a parent polymerase to introduce mutations for generating a library of mutants. Polymerases obtained from thermophlic organisms such as *Thermus aquaticus* have particularly desirable enzymatic characteristics due to their stability and activity at high temperatures. Thermostable polymerases are stable and retain activity at temperatures greater than about 37° C., generally greater than about 50° C., and particularly greater than about 90° C. The use of the thermostable polymerase Taq DNA polymerase I as a parent polymerase to generate polymerase mutants is disclosed herein in the Examples.

In addition to creating mutant DNA polymerases from organisms that grow at elevated temperatures, the methods of the invention can similarly be applied to non-thermostable polymerases provided that there is a selection or screen such as the genetic complementation of a conditional polymerase mutation. Such a selection or screen of a non-thermostable polymerase can be, for example, the inducible of repressible expression of an endogenous polymerase. Polymerases having altered fidelity or altered catalytic activity can similarly be generated and selected from both prokaryotic and eukaryotic cells as well as viruses.

Those skilled in the art will know how to apply the teachings described herein to the generation of polymerases having altered fidelity from such other organisms and such other cell types.

Although a specific embodiment using Taq DNA polymerase I is disclosed in the examples, the methods of the invention can similarly be applied to DNA polymerases other than *Thermus aquaticus* DNA polymerases. Such other polymerases include, for example, *Escherichia coli*, Mycobacterium, Rickettsia, Bacillus, Chlamydia, Chlamydophila, Chloroflexus, Haemophilus, Helicobacter, Lacococcus, Methylobacterium, Streptococcus, Streptomyces, Synechocysts, Aquifex, Borielia, Rhodothermus, and Treponema. Using the guidance provided herein in reference to Taq DNA polymerases, those skilled in the art can apply the teachings of the invention to the generation and identification of these other polymerases having altered fidelity of polynucleotide synthesis.

Thus, the invention provides a general method for the production of a DNA polymerase mutant that has an altered fidelity or an altered catalytic activity in DNA synthesis. The altered polymerase fidelity can be either an increase or a decrease in the accuracy of DNA synthesis. An example of a preferred DNA polymerase mutant has an altered substrate specificity.

In one embodiment, the invention involves the production of a population nucleic acids encoding a polymerase with altered motif A and introduction of the population into host cells to produce a library. The mutagenized polymerase encoding nucleic acids are expressed, and the library is screened for active polymerase mutants by complementation of a temperature sensitive mutation of an endogenous polymerase. Colonies which are viable at the non-permissive temperature are those which have polymerase encoding nucleic acids which code for active mutants.

The modified gene or gene fragment can be recovered from the plasmid, or phage by conventional means and ligated into an expression vector for subsequent culture and purification of the resulting enzyme. Numerous cloning and expression vectors, including mammalian and bacterial systems, are suitable for practicing the invention, and are described in, for example, Sambrook et al., Molecular Cloning: A Laboratory Manual, second edition, Cold Spring Harbor, 1989. Those of skill in the art will recognize that the mutant DNA polymerases with different activities from the wild type enzyme are most easily constructed by recombinant DNA techniques. When one desires to produce one of the mutant enzymes of the present invention, or a derivative or homologue of those enzymes, the production of a recombinant form of the enzyme typically involves the construction of an expression vector, the transformation of a host cell with the vector, and culture of the transformed host cell under conditions such that expression will occur. Means for preparing expression vectors, transforming and culturing transformed host cells are well known in the art and are described in detail in, for example, Sambrook et al., 1989, supra.

To generate a random population of polymerase mutants, a random sequence of nucleotides is substituted for motif A sequence of a plasmid-encoded gene that specifies a DNA polymerase. In one application of this procedure, a partial double-stranded DNA is created with 3' recessed-ends by hybridizing a first oligodeoxyribonucleotide containing a defined sequence with a restriction site "X". This first oligodeoxyribonucleotide is hybridized to a second oligodeoxyribonucleotide, which contains a nucleotide sequence complementary to the defined sequence and a partially randomized sequence encoding amino acids of interest. The second oligodeoxyribonucleotide additionally contains a restriction site "Y". The partially double-stranded oligonucleotide is filled in by DNA polymerase, cut at restriction sites "X" and "Y", and ligated into a vector. After ligation, the reconstructed plasmids constitute a library of different nucleic acid sequences encoding the thermostable DNA polymerase and polymerase mutants.

A genetic screen can be used to identify active polymerase mutants. For example, the library of nucleic acid sequences encoding Taq DNA polymerase and polymerase mutants are transfected into a bacterial strain such as *E. coli* strain recA718 polA12, which contains a temperature sensitive mutation in DNA polymerase. Exogenous DNA polymerases have been shown to functionally substitute for *E. coli* DNA polymerase I using *E. coli* strain recA718 polA12 and to complement the observed growth defect at elevated temperature, presumably caused by the instability of the endogenous DNA polymerase I at elevated temperatures (Sweasy and Loeb, *J. Biol. Chem.* 267:1407–1410 (1992); Kim and Loeb, *Proc. Natl. Acad. Sci USA* 92:684–488 (1995)). Using a complementation system, which employs a randomly mutated Taq library to complement the growth defect of *E. coli* strain recA 718 polA12, Taq DNA polymerase I mutants are identified in host bacteria that harbor plasmids encoding active thermoresistant DNA polymerases that allow bacterial growth and colony formation at elevated or restrictive temperatures.

In addition, active and thermostable mutants can be identified by lysing thermolabile bacteria host (e.g. *E. coli*) and analyzing directly for DNA polymerase activity at elevated temperatures. For example, active Taq polymerase mutants can be screened for the ability to synthesize DNA (e.g., by incorporating radioactive nucleotides) at an elevated temperature. This method can be expanded for screening other active thermostable enzyme mutants expressed in thermolabile hosts. In the method, individual mutants from a random library are expressed in thermolabile hosts. Colonies of *E. coli* harboring a unique mutant protein of interest are propagated at 37° C. The mutant protein is partially purified by heat denaturing and lysing the host bacteria at elevated temperatures such as 95° C. Following centrifugation, the supernatant containing partially purified thermostable protein of interest can be collected and tested for a specific activity of the protein. In our studies with various enzymes, we have identified that 5–10% of random mutants containing substitutions within the catalytic site are active. Thus, this screen method is potentially useful for many thermostable protein.

The production of mutant DNA polymerases with active enzymatic activities may also be accomplished by processes such as site-directed mutagenesis. See, for example, Sambrook et al., Molecular Cloning: A Laboratory Manual, Cold Spring Harbor, 1989, second edition, Chapter 15.51, "Oligonucleotide-Mediated Mutagenesis," which is incorporated herein by reference. Site-directed mutagenesis is generally accomplished by site-specific primer-directed mutagenesis. This technique is now standard in the art and is conducted using a synthetic oligonucleotide primer complementary to a single-stranded phage DNA to be mutagenized except for a limited mismatch representing the desired mutation. Briefly, the synthetic oligonucleotide is used as a primer to direct synthesis of a strand complementary to the plasmid or phage, and the resulting double-stranded DNA is transformed into a phage-supporting host bacterium. The resulting bacteria can be assayed by, for example, DNA sequence analysis or probe hybridization to identify those plaques carrying the desired mutated gene sequence. Alternatively, "recombinant PCR" methods can be employed (Innis et al. editors, PCR Protocols, San Diego, Academic Press, 1990, Chapter 22, Entitled "Recombinant PCR", Higuchi, pages 177–183).

The fidelity of active polymerase mutants can be determined by several methods. The active polymerases can be, for example, screened for altered fidelity from crude extracts of bacterial cells grown from the viable colonies. In one method, a primer extension assay is used with a biased ratio of nucleoside triphosphates consisting of only three of the nucleoside triphosphates. Elongation of the primer past template positions that are complementary to the deleted nucleoside triphosphate substrate in the reaction mixture results from errors in DNA synthesis. Processivity of high fidelity polymerases will terminate when they encounter a template nucleotide complementary to the missing nucleoside triphosphate whereas the low fidelity polymerases will be more likely to misincorporate a non-complementary nucleotide. The accuracy of incorporation for the primer extension assay can be measured by physical criteria such as by determining the size or the sequence of the extension product. This method is particularly suitable for screening for low fidelity mutants since increases in chain elongation are easily and rapidly quantitated.

A second method for determining the fidelity of polymerase mutants employs a forward mutation assay. A template containing a single stranded gap in a reporter gene such as lacZ is used for the forward mutation assay. Filling in of the gapped segment is carried out by crude heat denatured bacterial extracts harboring plasmids expressing a thermostable DNA polymerase mutant. For determining low fidelity polymerase mutants, reactions are carried out in the presence of equimolar concentrations of each nucleoside triphosphate. For determining high fidelity polymerase mutants, the reaction is carried out with a biased pool of nucleoside triphosphates. Using a biased pool of nucleoside-triphosphates results in incorporation of errors in the synthesized strand that are proportional to the ratio of non-complementary to complementary nucleoside triphosphates in the reaction. Therefore, the bias exaggerates the errors produced by the polymerases and facilitates the identification of high fidelity mutants. The fidelity of DNA synthesis is determined from the number of mutations produced in the reporter gene.

Procedures other than those described above for identifying and characterizing the fidelity of a polymerase are known in the art and can be substituted for identifying high or low fidelity mutants. Those skilled in the art can determine which procedures are appropriate depending on the needs of a particular application.

Our results counter the common paradigm that amino acid substitutions within the catalytic site lead to reduced stability and enzymatic activity. Our genetic selection protocol allows isolation of mutant polymerases that retain a high DNA polymerase activity. Bacteria dependent on these polymerases can be grown under logarithmic conditions in liquid broth (prior to plasmid isolation and protein purification) or as colonies in solid agar at 37° C. (>50 generations) without significant variations in growth kinetics. Thus bacteria dependent on mutant enzymes for survival are fit to replicate repetitively. Mutant DNA polymerases may offer selective advantages such as: ability to resist incorporation of chain terminating nucleotide analogs, increased catalytic activity, ability to copy through hairpin structures, increased processivity, and altered fidelity. For example, some mutants in our library are more active than WT Taq pol I, and some mutants exhibit enhanced fidelity. Some mutants can incorporate chemotherapy drugs such as ara-C and acyclovir 100 times more efficiently than wt Taq pol I.

We find, following random sequence mutagenesis and selection by genetic complementation, that amino acids of the polymerase active site are highly mutable. Our studies produced highly active enzymes. Preservation of a plastic, mutable active site could facilitate the generation of beneficial mutants under specific selective forces such as mutant polymerases able to transiently incorporate ribonucleotides or their analogs under conditions of dNTP deprivation during nucleotide-based therapy. Such ribonucleotide analogs include ara-C, acyclovir, or other antiviral or anti-cancer drug. In addition, the plastic nature of active sites may allow proteins to tolerate high mutation burdens. It has been demonstrated that as few as three successive selection steps yielded a population of $E.$ $coli$ cells that mutated at elevated rates (Mao, et al., $J.$ $Bacteriol.$ 179:417–422 (1997)), and 1–5% of pathogenic $E.$ $coli$ and $Salmonella$ $enterica$ are mutators (LeClerc, et al., $Science$ 274:1208–11 (1996)). Enrichment for mutator cells under adverse conditions could account for the generation of a mutator phenotype during cancer progression (Loeb, $Science$ 277:1449–150 (1997)). In addition, exponential growth of recombination-incompetent $E.$ $coli$ after four years yields populations with heterogeneous genotypes (Elena, et al., $Science$ 272:1802–4 (1996)).

GenBank sequence alignment analysis of over 20 polA genes from different organisms show that a large majority of the organisms have retained the DYSQIELR motif within the pol I active site, and species within a genus have retained up to 90% sequence identity for the entire polymerase gene. Thus, DNA polymerase sequence appears to be homogeneous after millions of generations. Amino acid sequence identity can be preserved by one of at least two mechanism. 1) WT amino acid sequence may have the highest over all fitness and thus selective advantage over mutated sequences, or 2) recombination-like mechanisms serve to preserve homogeneous sequences. The predominance of one mechanism over the other can be differentiated by examining the nucleotide sequence in addition to the amino acid sequence. Selection of WT amino acid sequence can lead to accumulation of silent mutations after prolonged evolution that encode for identical amino acids. In contract, if horizontal transfer of genetic material serves to preserve homogeneous amino acid sequences, then the nucleotide sequences should also be homogeneous. Sequence alignments of $E.$ $coli$ polA gene encoding DNA polymerase I from distinct strains (K-12 and B) dividing independently for many years and related species within the same genus (e.g. $Thermus$ $acquaticus$ and $Thermus$ $thermophilus;$ $Mycobacterium$ $tuberculosis$ and $Mycobacterium$ $smegmatis;$ Rickettsia) which have been evolving separately for many years show each member has nearly identical nucleotide sequence. Thus, related organisms have maintained relatively homogeneous genomes after many million divisions. From this information, a more detailed model of punctuated evolution would allow for: 1) Growth during adverse conditions selects for populations of mutators; 2) Inherent plasticity of proteins we describe here enables tolerance of the high mutation burden during adverse conditions and the generation of mutations with a selective advantage; 3) Following successful survival through periods of adverse conditions, WT sequence (one that is fit and the most prevalent) is generated through horizontal transfer.

The following examples are offered by way of illustration only and are by no means intended to limited the scope of the claimed invention.

EXAMPLES

Example 1
Preparing Plasmids Containing Substituted Random DNA Sequences From Leu605 to Arg617 of *Thermus aguaticus* DNA Polymerase I Taq pol was cloned into low copy (1 to 3 copies/cell) pHSG576 vector containing a *E. coli* pol I independent origin of replication, SCO101. A silent BisWI site was created in Taq pol I by site directed mutagenesis (C to A) at position 1758 (pTaq). A nonfunctional stuffer vector (pTaqDUM) was constructed by cloning two hybridized oligos into pTaq between BisWI and SacII sites; these two restriction sites flank the sequence encoding for Motif A. A random library (pTaqLIB) was created by preparing a randomized oligo with a BisWI site in which nucleotides encoding amino acids Leu605 to Arg 617 contained 88% wild-type and 4% each of the other three nucleotides. This oligo was hybridized with an oligonucleotide primer containing SacII site in equimolar proportions, and T7 DNA polymerase (exo-) was used to copy the template containing the randomized nucleotides. The double-stranded oligo was digested with BisWI and SacII, purified, and inserted into pTaqDUM between BisWI and SacII restriction sites in place of the stuffer fragment. The reconstructed plasmids were transformed into DH5 cells by electroporation, and the cells were incubated in 1 mL 2×YT (yeast Tryptone media) at 37° C. for 1 hour. The number of clones within the library was determined by plating an aliquot onto 2×YT plates containing 30 $\mu$g/mL chloramphenicol. The remainder of the transformation mixture was pooled and incubated in 1 L of 2×YT containing chloramphenicol for 12 hours at 37° C. Plasmids were purified (pTaqLIB) by CsCl gradient centrifugation.

Example 2
Selecting Active Clones By Genetic Complementation

In complementation studies, *E. coli* recA 718polA12 cells were used. This *E. coli* strain, which contains a temperature sensitive mutation in polA gene encoding DNA polymerase I, forms colonies at 30° C., but not at 37° C. The *E. coli* recA 718polA12 cells were transformed with 0.2 $\mu$g each of the following plasmids: pHSG576, pTaqDUM, pTaq, or pTaqLIB by electroporation, and the cells were allowed to recover in nutrient broth medium for 2 hours at 30° C. Following recovery, a small fraction of the mixture was plated in duplicate onto nutrient agar plates containing chloramphenicol; one plate was incubated at 30° C. and the other at 37° C. for 24 hrs, and resulting colonies were counted. Only paired samples that contained 200 colonies or less at 30° C. were analyzed, because dense plating of cells leads to elevated background at 37° C. Complementation experiments with either inactive pHSG576 or pTaqDUM consistently yielded over 100-fold fewer colonies at 37° C. relative to 30° C., indicating that the background for our complementation-based section assay <1%. Transformation with pTaq consistently yields equal number of colonies after incubations at 30 or 37° C., indicating that Taq pol I fully restores the growth defective phenotype at the elevated temperatures, of 37° C.

We constructed a randomly mutated Taq library containing 200,000 independent clones, and 5% of the transformed *E. coli* recA 718 polA12 formed colonies at 37° C. relative to 30° C. After subtracting the background (<1%), we estimate there are 8,000 to 10,000 independent library clones that encode an active Taq pol I. This alone suggests that the polymerase catalytic site can potentially accommodate a surprisingly large number of amino acid substitutions in vivo.

Example 3
Sequencing the Randomized Insert From Unselected Clones

To establish the spectrum of mutations that restored growth of *E. coli* recA 718 polA12, we sequenced the randomized insert from both unselected clones (30° C.) and from selected clones (37° C.). Plasmids harboring WT and mutant Taq pol Is were isolated by minipreps (Promega) after overnight propagation at 37° C. in 2×YT, and 200 nts surrounding the randomized region were amplified by PCR and sequenced. Analysis of sequences from unselected plasmids, which reflects the distribution of mutants found in the random library prior to selection, shows that the average number of amino acid (amino acid) substitution is 4.

Of the 26 unselected clones we sequenced, 3 clones have 2 amino acid substitutions; 4 clones have 3 aa changes, 7 have 4 aa changes, 4 have 5 aa changes, 1 has 7aa changes; 1 contains an insertion, 4 contain deletions, and 2 are pTacDUM.

Example 4
Sequencing and Measuring Activities From Selected Clones

After selection, we randomly picked 350 colonies that grew at 37° C., measured the Taq DNA polymerase activity, isolated the plasmids and sequenced 200 nucleotides encompassing the substituted random sequence.

The 350 colonies that grew on 37° C. plates were isolated and grown in nutrient broth individually overnight at 30° C. Each culture was grown to O.D. of 0.3 at 30° C. in 10 mL and Taq pol I expression was induced with 0.5 mM IPTG and incubations continued for 4 hours. Taq pols were partially purified using a modified protocol of refs. (Grimm, et aL, *Nucleic Acids Res* 23:4518–9 (1995), Desai, et al., *Biotechniques* 19:780–2, 784 (1995)), which allows efficeint (>50% purfication of Taq I while removing endogenous polymerase and nuclease activities. Polymerase activity was assayed using a 20 $\mu$L reaction mixture containing 50 mM KCl, 10 mM Tris-HCl (pH 8), 0.1% Triton-X, 2.5 mM MgCl$_2$, 0.4 mg activated calf thymus DNA, 10 $\mu$M each dNTP, 0.25 mCi [-$^{32}$P]dATP, and 1 $\mu$L of partially purified WT or mutant Taq pols. Incubations were at 72° C. for 5 min and reactions were stopped with the addition of 100 $\mu$L 0.1 M sodium pyrophosphate, followed by 0.5 mL 10% TCA. Polymerase activity was quantified by collecting precipitated radioactive DNA onto glass filter papers, and amount of radioactive counts were measured by scintillation.

Of the 350 clones, 20 were inactive (<2% DNA polymerase activity relative to WT); 39 clones had low activity (2 to 10%) and/or thermostability; while 291 were active (>10 to 200% WT activity). The 291 independent active clones had on average 2 amino acid changes, ranging from no amino acid changes (27 clones) to one clone containing 6 amino acid changes; two clones have ambiguous sequences. Taq pol I from the 27 plasmids that encode WT enzyme at the same amino acid sequence (yet containing silent nucleotide changes) have similar DNA polymerase activity relative to WT controls. The preparations from pTaqDum and pHSG negative controls yield <1% of WT polymerase activity. Of the 60 mutants with a single amino acid change, 60% (36 mutants) are highly active (>66% to 200% WT activity). In comparison, 27% (24 out of 90 mutants) with 2 amino acid changes, 20% (14 out of 70 mutants) with 3 amino acid changes, 22% (7 out of 32) with 4 amino acid changes, 11% (1 out of 9) with 5 amino acid changes and a single mutant with 6 amino acid changes, were all highly active. Thus, even in cases of especially pronounced mutation burden with one-third to one-half of an evolutionarily conserved motif altered, a large number of mutants exhibit high activity. These 263 clones containing 1 to 6 amino acid substitutions represent a large collection of physiologically active polymerase mutants.

Sequence analysis of all 291 selected active clones (10 to 200% WT activity, FIG. 2A), including 87 most active mutants (>66% to 200% WT activity, FIG. 2B), showed that most Motif A residues tolerated a wide spectrum of substitutions (Leu605, Leu606, Val607, Ala608, Leu609, Ser612, Ile614, and Arg617), some residues tolerated conservative substitutions (Tyr611, Gln613, Glu615, and Leu 616), and only one residue was immutable (Asp610). One of the highly mutable residues, Ser612, tolerated substitutions that were diverse in size and hydrophilicity while often preserving WT-like activity. A mutant with 6 substitutions (Leu605Arg, Leu606Met, Val607Lys, Ala608Ser, Leu609Ile, and Ser612Arg) exhibited WT DNA polymerase activity. Analysis of 59 mutants with a single amino acid change (FIG. 2C) yielded a similar distribution of mutability and allowed us to determine the effect on activity conferred by specific amino acid substitutions. Leu605Arg conferred greater polymerase activity relative to WT Taq pol I (150%), and all selected Leu605Arg mutants occurring in context of multiple mutations also exhibited high activity (FIG. 2A and 2B). The single substitution, Arg617Phe, confers twice the activity of WT Taq Pol I, while other substitutions at this locus lowered Taq pol I activity (FIG. 2C).

Example 5

Screening Selected Slones For the Ability to Incorporate Ribonucleotides

To determine if alterations within the catalytic site can confer other properties on a DNA polymerase and lead to alterations in the substrate specificity, we screened all 291 selected clones for the ability to incorporate ribonucleotides.

Each of the selected Taq pols that retain at least 10% activity relative to WT enzyme at 72° C. (291 total) were tested for the ability to incorporated ribonucleotides. Primer/template constructs were prepared by hybridizing 5'-$^{32}$P end-labeled 23mer primer (5' cgc gcc gaa ttc ccg cta gca at, SEQ ID NO: 35) with 46 mer template (5'-gcg cgg aag ctt ggc tgc aga ata ttg cta gcg gga att cgg cgc g, SEQ ID NO: 36) using a 1:2 primer to template ratio. The primer/template (5 nM) was incubated in the presence of 50 mM KCl,10 mM Tris-HCl (pH 8), 0.1% Triton-X, 2.5 mM MgCl$_2$,and 1 µL of partially purified Taq pols (0.1 to 0.01 units) in 10 µL volumes in the presence of 0 to 250 µM each rNTPs. Reactions were terminated after 30 min incubation at 55° C. with the addition of 2 µL of formamide containing stop solution (Amersham). Products were analyzed by 14% denaturing PAGE.

This screen identified a small subset of mutants (23 out of 291) that can incorporate rNTPs efficiently (Table 2). These 23 mutants fall into two major classes: 1) Those encoding a hydrophilic substitution at Ile614; these enzymes constitute the majority of rNTP incorporating mutants with 1 or 2 substitutions, and 2) those that encode a Glu615Asp substitution; these enzymes contain 1–3 other substitutions.

Example 6

Purifying Wild Type and Mutant Tag Polymerase

Wild type and mutant (#94, #265, and #346; Table 2) Taq pols were purified to homogeneity using a modified procedure according to Engelke, et al., (*Anal Biochem* 191: 396–400 (1990)). Step 1: Bacteria cultures (DH5α cells; 2L) harboring pTaq or selected mutant pTaqLIB plasmid were harvested and lysed in the presence of buffer A (30 mM Tris-HCl, pH 7.9, 50 mM glucose, 1 mM EDTA, 0.5 mM phenylmethylsulfonyl fluoride, 0.5% Tween 20, 0.5% Nonident P40) with lysozyme (4 mg/mL) with repetitive freezing and thawing at −70° C. and 70° C. Step 2: Taq pol was precipitated by the addition of polyethyeneimine at a final concentration of 0.1%; recovered by centrifugation and washed with buffer containing low salt (0.025 M KCl ) buffer C (20 mM HEPES, pH 7.9, 1 mM EDTA, 0.5 mM PMSF, 0.5% Tween 20,0.5% NonidentP40), and then solubilized in 0.15 M KCl buffer C. Step 3: The enzyme was diluted to 50 mM KCl and loaded onto a pre-equilibrated HiTrap Heparin 5 mL column at 1 mL per min flow rate. The column was washed with 10 volumes of Buffer C (50 mM KCl), and protein eluted using a linear gradient 50 mM to 750 mM KCl (60 mL). Fractions (1 mL) were assayed for polymerase activity by measuring incorporation of [α$^{32}$P] dGTP at 70° C. using activated calf thymus DNA as a template with Mg$^{2+}$ and all four dNTPs including [α$^{32}$P] dGTP. Peak fractions with WT and mutant enzymes consistently eluted at approximately 300 mM KCl, and were stored in 20% glycerol at −70° C.

Example 7

Kinetic Analysis of WT and Mutant Taq pol I on Incorporating Ribonucleotide and Deoxyribonucleotide The efficiencies of purified WT, mutant #94, 265 and 346 Taq pol I for incorporating dNTP and rNTP were determined by the following protocol. A 46mer template (5'-ccc ggg aaa ttt ccg gaa ttc cga tta ttg cta gcg gga att cgg cgc g, SEQ ID NO:37) was hybridized onto one of four $^{32}$P-labeled primers: 23 mer (5'-cgc gcc gaa ttc ccg cta gca at, SEQ ID NO: 35), 24mer (5'-cgc gcc gaa ttc ccg cta gca ata, SEQ ID NO: 38), 25 mer (5'-cgc gcc gaa ttc ccg cta gca ata t, SEQ ID NO: 39) or 26 mer (5'-cgc gcc gaa ttc ccg cta gca ata tc, SEQ ID NO: 40). The steady-state Michaelis-Menten parameters k$_{cat}$ and K$_m$ were calculated by incubations with limiting amounts of Taq pol in the presence of 5 nM primer/template and varying concentration of each dNTP or rNTP for 10 minutes at 55° C. as described in Boosalis, et al. (*J. Biol. Chem.* 262:14689–14699 (1987)). All products were analyzed by 14% PAGE and quantified by phosphorimager analysis.

Kinetic analysis showed that purified WT Taq pol I did not efficiently incorporate ribonucleotides. WT Taq Pol I incorporated dG, dA and dC up to 30,000 times more efficiently (k$_{cat}$/K$_m$) than the respective ribonucleotides, and this difference was largely attributable to differences in K$_m$ (Table 3). Taq pol I incorporated noncomplementary nucleotides at a rate of 1 for each 9000 complementary deoxynucleotides polymerized. (Tindall, et al., *Biochemistry* 27:6008–6013 (1988)). Thus, Taq pol I is more efficient at excluding ribonucleotides than excluding noncomplementary deoxynucleotides. The active site is especially adept at selecting dTTP over rUTP, incorporating dTTP 10$^6$ fold more efficiently relative to rUTP. These data suggest DNA polymerases have evolved a sophisticated mechanism to exclude ribonucleotides, especially uracil, from its catalytic site. In contrast, kinetic analysis of mutants (#94, 265 and 346) purified to homogeneity showed that each polymerase incorporated rG, rA, and rC at an efficiency approaching up to ¹⁄₁₀th that of the corresponding dNTP (Table 3). These mutants incorporated each ribonucleotide up to three orders of magnitude more efficiently than the WT polymerase.

TABLE 3

Efficiency of dNTP and rNTP incorporation by WT and several mutant Taq pol I

| Protein | Nucleotide | dNTP | | | rNTP | | | dNTP/rNTP |
|---|---|---|---|---|---|---|---|---|
| | | $k_{cat}$ (s$^{-1}$) | $K_m$ (M) | $k_{cat}/K_m$ | $k_{cat}$ (s$^{-1}$) | $K_m$ (M) | $k_{cat}/K_m$ | Discrimination* |
| wild type | G | 0.020 | 0.021 | 1.0 | 0.0026 | 76 | 3.5 × 10$^{-5}$ | 29,000 |
| | A | 0.012 | 0.070 | 0.17 | 0.016 | 230 | 7.0 × 10$^{-6}$ | 24,000 |
| | C | 0.013 | 0.042 | 0.31 | 0.00083 | 59 | 1.4 × 10$^{-5}$ | 22,000 |
| | T/U | 0.013 | 0.0050 | 2.6 | 0.00043 | 240 | 1.8 × 10$^{-6}$ | 1,400,000 |
| Mutant 94 | G | 0.0058 | 0.086 | 0.067 | 0.0065 | 0.94 | 0.0070 | 10 |
| (A608S, I614N) | A | 0.012 | 0.15 | 0.080 | 0.0065 | 6.7 | 0.00097 | 83 |
| | C | 0.0058 | 0.089 | 0.065 | 0.0075 | 14 | 0.00054 | 120 |
| | T/U | 0.0071 | 0.022 | 0.32 | 0.0067 | 31 | 0.00022 | 1,500 |
| Mutant 265 | G | 0.015 | 0.0071 | 2.1 | 0.012 | 0.77 | 0.016 | 130 |
| (I614N, L616I) | A | 0.014 | 0.048 | 0.29 | 0.0080 | 4.4 | 0.0018 | 160 |
| | C | 0.015 | 0.034 | 0.44 | 0.0073 | 6.2 | 0.0012 | 370 |
| | T/U | 0.016 | 0.016 | 1.0 | 0.017 | 35 | 0.00049 | 2100 |
| Mutant 346 | G | 0.0020 | 0.12 | 0.017 | 0.0056 | 1.7 | 0.0032 | 5.3 |
| (A608D, E615D) | A | 0.0040 | 0.20 | 0.020 | 0.0040 | 26 | 0.00015 | 130 |
| | C | 0.0020 | 0.29 | 0.0069 | 0.0036 | 5.4 | 0.00067 | 10 |
| | T/U | 0.0087 | 0.018 | 0.48 | — | — | — | — |

Figure 3:
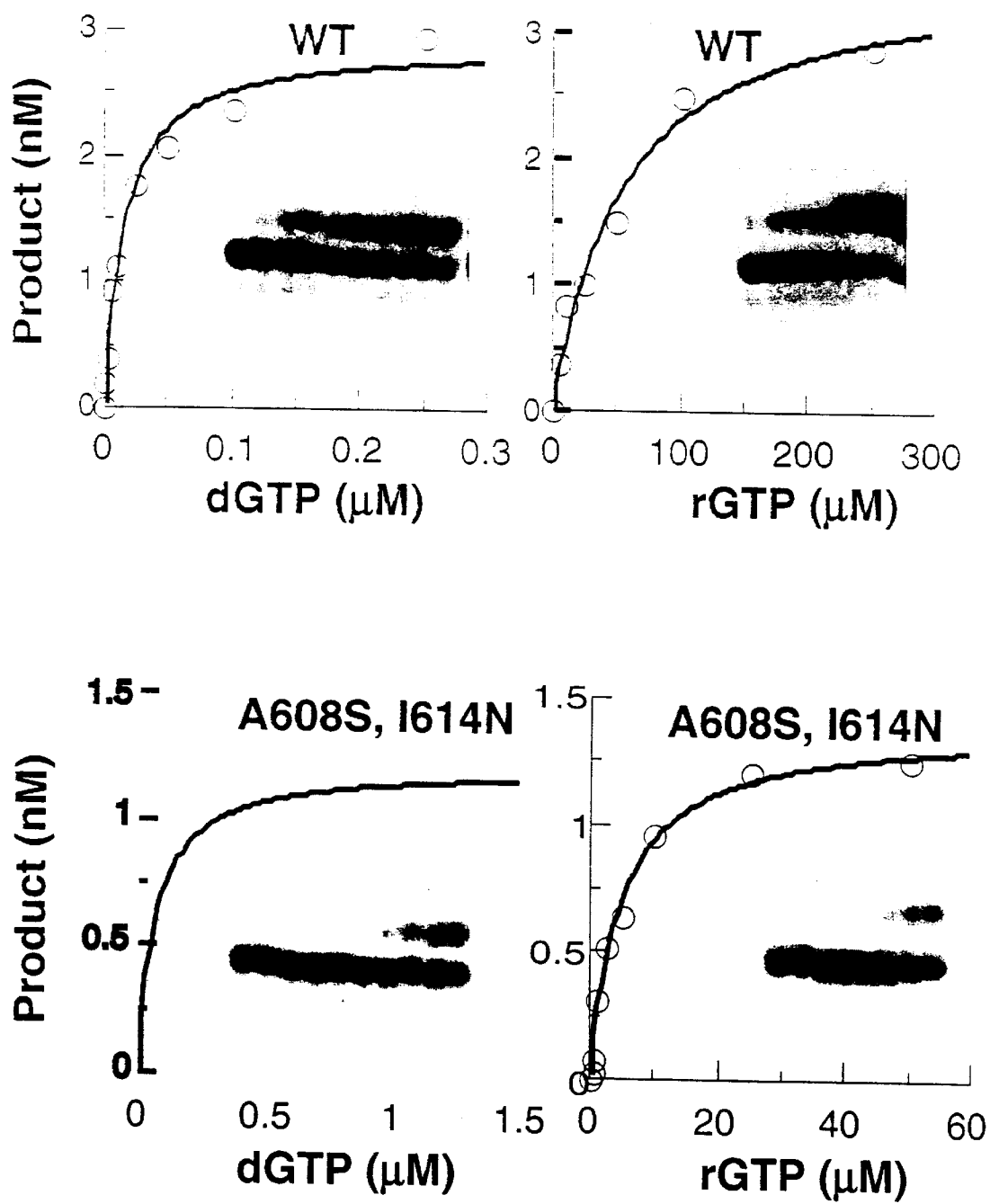
FIG. 3 compares the efficiency of dGTP and rGTP incorporation by WT and Mutant #94.

*dNTP/dNTP discrimination equals efficiency of dNTP incorporation ($k_{cat}/K_m$) relative to rNTP incorporation Example 8
Comparing the Efficiency of dGTP and rGTP Incorporation By WT and a Mutant WT Taq pol I (0.3 fmol/μL for dNTP reactions and 3 fmol/μL for rNTP reactions) or mutant #94 (A6085, I614N; 0.2 fmol/μL for both dNTP and rNTP reactions) was incubated with 26mer/46mer (primer/template; 5 nM) with increasing concentration of either dGTP or rGTP for 10 min at 55° C. in 10 μL reactions. Product yield was quantified by phosphoimagery. The $k_{cat}/K_m$ values obtained upon a hyperbolic curve fit of the plots reflects the efficiency of nucleotide incorporation. The results in FIG. 3 showed that incorporation of rGTP relative to dGTP resulted in a product with a slower electrophoretic migration.

Example 9
Determining the RNA Polymerase Activity of WT and Mutants

Figure 4:
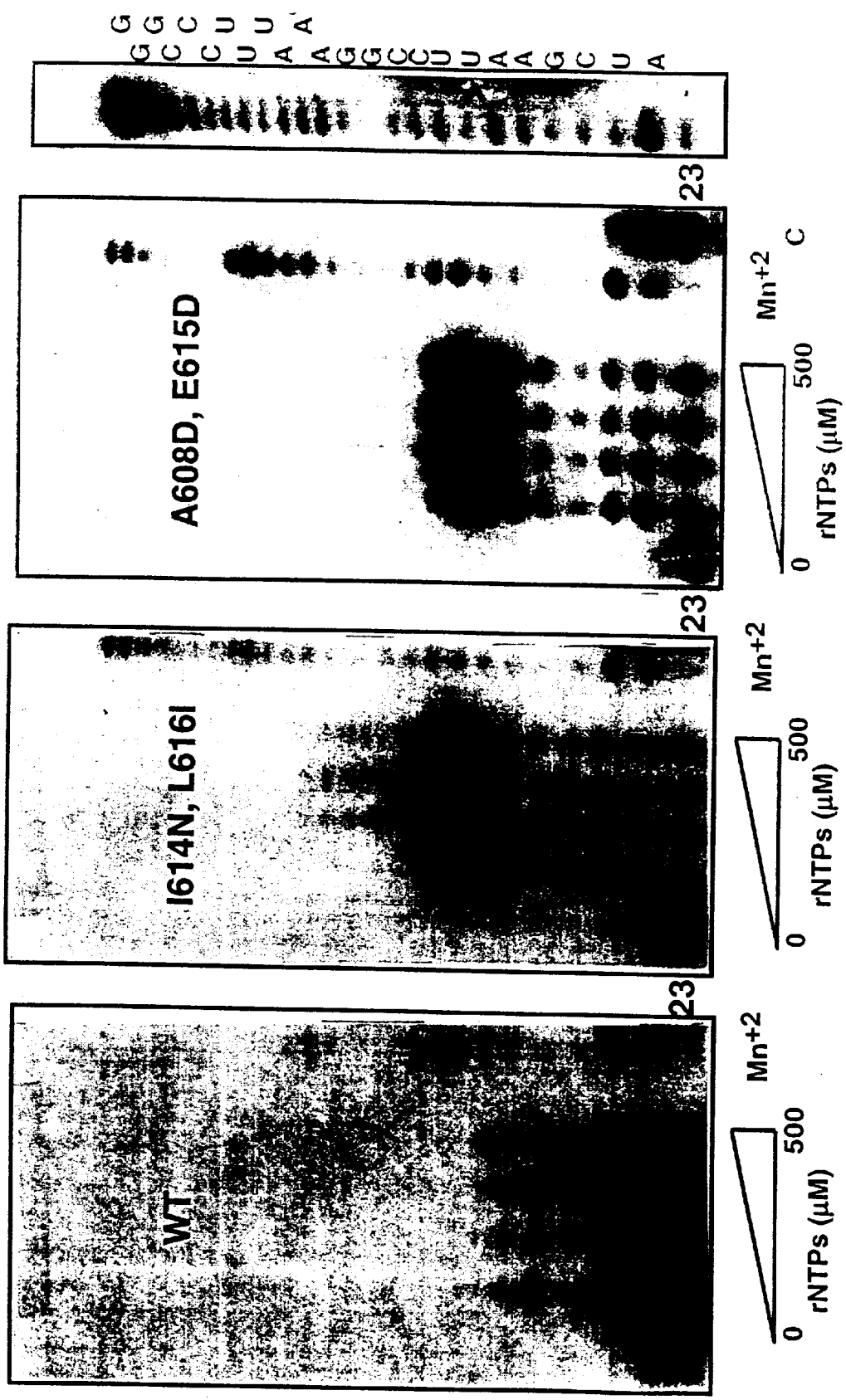
FIG. 4 shows polymerization in the presence of all 4 rNTPs with WT Taq pol I (30 fmol/μL), mutant #265 (I614N and L616I; 20fmol/μL) and mutant #346 (A608D and E 615D; 20 fmol μL). Incubation (10 μL) with each polymerase was conducted for 10 mins at 55° C. with increasing amounts of all 4 rNTPs (0, 50, 100, 250, or 500 μM each), 23mer/46mer dsDNA (primer/template; 5 nM), and 2.5 mM $MgCl_2$. Incubations with $Mn^{+2}$ and subsequently incubated with 0.25 N NaOH for 10 minutes at 95° C. DNA ladder products resulted from incubation of thermosequenase (mutant Taq pol I) in the presence of ddNTP/dNTP mix (Amersham).

To determine if polymerases can function as RNA polymerases by incorporating multiple ribonucleotides sequentially, we incubated purified WT Taq pol I, mutant #265 (I614N and L616I), and mutant #346 (A608D and E615D), in the presence of increasing amounts of all four rNTPs (FIG. 4). While the WT enzyme inefficiently incorporated and extends ribonucleotides, both mutant enzymes polymerized multiple ribonucleotides, even at rNTP concentrations well below that found in cells. The strong pause sites produced at runs of template dAs was exactly what one would predict from the kinetic data (Table 3), demonstrating decreased efficiency of UTP incorporation. Extension past these runs was facilitated by increasing incubation time or increasing ribonucleotide concentrations. With Mn$^{+2}$ as the metal cofactor, elongation proceeded up to the 5' end of the template even in presence of low rNTP levels. In control incubations the elongated products were degraded in alkali to regenerate the initial substrate, illustrating the products were RNAs.

Although the invention has been described with reference to the presently preferred embodiments, it should be understood that various modifications can be made without departing from the spirit of the invention.

What is claimed is:

1. A mutant DNA polymerase within the Pol I family of polymerases comprising a mutation in an active site of a naturally occurring DNA polymerase, wherein said active site comprises an amino acid sequence of DYSQIELR (SEQ ID NO: 2), said mutation comprises an alteration of an amino acid other than E in said sequence, and said mutant DNA polymerase possesses altered fidelity or altered catalytic activity in comparison with said naturally occurring DNA polymerase.

2. The mutant DNA polymerase according to claim 1, wherein said D of said amino acid sequence motif is not altered in said mutant form.

3. The mutant DNA polymerase according to claim 1, wherein said mutant DNA polymerase incorporates a ribonucleotide at a rate at least 10 fold greater than that of said naturally occurring DNA polymerase.

4. The mutant DNA polymerase according to claim 3, wherein said mutation comprises an alteration of I in said amino acid sequence.

5. The mutant DNA polymerase according to claim 3, wherein said I is altered to a hydrophilic amino acid in said mutant form.

6. The mutant DNA polymerase according to claim 3, wherein said mutation comprises two or more amino acid substitutions in said amino acid sequence.

7. The mutant DNA polymerase according to claim 3, wherein said mutant DNA polymerase functions as both DNA polymerase and RNA polymerase.

8. The mutant DNA polymerase according to claim 1, wherein said polymerase incorporates an unconventional nucleotide at a rate at least 10 fold greater than that of said naturally occurring DNA polymerase.

9. The mutant DNA polymerase according to claim 8, wherein said unconventional nucleotide is a ribonucleotide analog.

10. The mutant DNA polymerase according to claim 8, wherein said unconventional nucleotide comprises a base labeled with a reporter molecule.

11. The mutant DNA polymerase according to claim 10, wherein said reporter molecule is a fluorophore or a hapten.

12. The mutant DNA polymerase according to claim 8, wherein said unconventional nucleotide is a chemotherapy drug.

13. The mutant DNA polymerase according to claim 12, wherein said chemotherapy drug is ara-C or acyclovir.

14. The mutant DNA polymerase according to claim 8, wherein said unconventional nucleotide is an antiviral drug or an anti-cancer drug.

15. The mutant DNA polymerase according to claim 1, which has an increased catalytic efficiency for incorporating deoxyribonucleotide over said naturally occurring DNA polymerase.

16. The mutant DNA polymerase according to claim 1, wherein said naturally occurring DNA polymerase is a thermostable Thermus species DNA polymerase.

17. The mutant DNA polymerase according to claim 16, wherein said Thermus species is *Thermus aqaticus*.

18. An isolated nucleic acid sequence encoding the mutant DNA polymerase according to claim 1.

19. A mutant DNA polymerase within the pol I family of polymerases, comprising a mutation in an active site of a naturally occurring DNA polymerase, wherein said active site comprises an amino acid sequence of DYSQIELR (SEQ ID NO: 2) said mutation comprises two or more amino acid substitutions in said sequence, and said mutant DNA polymerase possesses altered fidelity or altered catalytic activity in comparison with said naturally occurring DNA polymerase.

20. The mutant DNA polymerase according to claim 19, wherein said D of said amino acid sequence motif is not altered in said mutant form.

21. The mutant DNA polymerase according to claim 19, wherein said mutant DNA polymerase incorporates a ribonucleotide at a rate at least 10 fold greater than that of said naturally occurring DNA polymerase.

22. The mutant DNA polymerase according to claim 21, wherein said mutation comprises an alteration of I in said amino acid sequence.

23. The mutant DNA polymerase according to claim 22, wherein said I is altered to a hydrophilic amino acid in said mutant form.

24. The mutant DNA polymerase according to claim 21, wherein said mutant DNA polymerase functions as both DNA polymerase and RNA polymerase.

25. The mutant DNA polymerase according to claim 19, wherein said polymerase incorporates an unconventional nucleotide at a rate at least 10 fold greater than that of said naturally occurring DNA polymerase.

26. The mutant DNA polymerase according to claim 25, wherein said unconventional nucleotide is a ribonucleotide analog.

27. The mutant DNA polymerase according to claim 25, wherein said unconventional nucleotide comprises a base labeled with a reporter molecule.

28. The mutant DNA polymerase according to claim 27, wherein said reporter molecule is a fluorophore or a hapten.

29. The mutant DNA polymerase according to claim 25, wherein said unconventional nucleotide is a chemotherapy drug.

30. The mutant DNA polymerase according to claim 29, wherein said chemotherapy drug is ara-C or acyclovir.

31. The mutant DNA polymerase according to claim 25, wherein said unconventional nucleotide is an antiviral drug or an anti-cancer drug.

32. The mutant DNA polymerase according to claim 19, which has an increased catalytic efficiency for incorporating deoxyribonucleotide over said naturally occurring DNA polymerase.

33. The mutant DNA polymerase according to claim 19, wherein said naturally occurring DNA polymerase is a thermostable Thermus species DNA polymerase.

34. The mutant DNA polymerase according to claim 33, wherein said Thermus species is *Thermus aqaticus*.

35. An isolated nucleic acid sequence encoding the mutant DNA polymerase according to claim 19.

* * * * *

UNITED STATES PATENT AND TRADEMARK OFFICE
CERTIFICATE OF CORRECTION

| | |
|---|---|
| PATENT NO. | : 6,329,178 B1 |
| DATED | : December 11, 2001 |
| INVENTOR(S) | : Premal H. Patel et al. |

It is certified that error appears in the above-identified patent and that said Letters Patent is hereby corrected as shown below:

<u>Column 1,</u>
Line 4, insert:
-- GOVERNMENT RIGHTS
This invention was made in part with government support under a National Institute of Health Grant 5R35CA39903. The government has certain rights to this invention. --

Signed and Sealed this

Twenty-third Day of April, 2002

*Attest:*

JAMES E. ROGAN
*Attesting Officer*  *Director of the United States Patent and Trademark Office*

SEQUENCE LISTING

<160> NUMBER OF SEQ ID NOS: 40

<210> SEQ ID NO 1
<211> LENGTH: 7
<212> TYPE: PRT
<213> ORGANISM: Thermus aquaticus
<220> FEATURE:
<221> NAME/KEY: VARIANT
<222> LOCATION: (7)...(7)
<223> OTHER INFORMATION: X= at position 7 is a valine residue (Val) or an isoleucine residue (Ile)

<400> SEQUENCE: 1

Ser Gln Ile Glu Leu Arg Xaa
1               5

<210> SEQ ID NO 2

```
<211> LENGTH: 8
<212> TYPE: PRT
<213> ORGANISM: Thermus aquaticus

<400> SEQUENCE: 2

Asp Tyr Ser Gln Ile Glu Leu Arg
1               5

<210> SEQ ID NO 3
<211> LENGTH: 13
<212> TYPE: PRT
<213> ORGANISM: Thermus aquaticus

<400> SEQUENCE: 3

Leu Leu Val Ala Leu Asp Tyr Ser Gln Ile Glu Leu Arg
1               5                   10

<210> SEQ ID NO 4
<211> LENGTH: 7
<212> TYPE: PRT
<213> ORGANISM: Esherichia coli

<400> SEQUENCE: 4

Tyr Ser Gln Ile Glu Leu Arg
1               5

<210> SEQ ID NO 5
<211> LENGTH: 7
<212> TYPE: PRT
<213> ORGANISM: Chlamydia trachomatis

<400> SEQUENCE: 5

Tyr Ser Gln Ile Glu Leu Arg
1               5

<210> SEQ ID NO 6
<211> LENGTH: 8
<212> TYPE: PRT
<213> ORGANISM: Mycobacterium tuberculosis

<400> SEQUENCE: 6

Asp Tyr Ser Gln Ile Glu Met Arg
1               5

<210> SEQ ID NO 7
<211> LENGTH: 8
<212> TYPE: PRT
<213> ORGANISM: Aquifex aeolicus

<400> SEQUENCE: 7

Asp Phe Ser Gln Ile Glu Leu Arg
1               5

<210> SEQ ID NO 8
<211> LENGTH: 8
<212> TYPE: PRT
<213> ORGANISM: Borrelia burgdorferi

<400> SEQUENCE: 8

Asp Tyr Ser Gln Ile Glu Leu Ala
1               5

<210> SEQ ID NO 9
<211> LENGTH: 8
<212> TYPE: PRT
```

```
<213> ORGANISM: Rhodothermus obamensis

<400> SEQUENCE: 9

Asp Tyr Val Gln Ile Glu Leu Arg
 1               5

<210> SEQ ID NO 10
<211> LENGTH: 8
<212> TYPE: PRT
<213> ORGANISM: Treponema pallidum

<400> SEQUENCE: 10

Asp Tyr Thr Gln Ile Glu Leu Tyr
 1               5

<210> SEQ ID NO 11
<211> LENGTH: 13
<212> TYPE: PRT
<213> ORGANISM: Eschericia coli

<400> SEQUENCE: 11

Leu Leu Val Ala Leu Asp Tyr Ser Gln Lys Glu Leu Arg
 1               5                  10

<210> SEQ ID NO 12
<211> LENGTH: 13
<212> TYPE: PRT
<213> ORGANISM: Eschericia coli

<400> SEQUENCE: 12

Leu Leu Val Ala Leu Asp Tyr Ser Gln Met Glu Leu Arg
 1               5                  10

<210> SEQ ID NO 13
<211> LENGTH: 13
<212> TYPE: PRT
<213> ORGANISM: Eschericia coli

<400> SEQUENCE: 13

Leu Leu Val Asp Leu Asp Tyr Ser Gln Met Glu Pro Arg
 1               5                  10

<210> SEQ ID NO 14
<211> LENGTH: 13
<212> TYPE: PRT
<213> ORGANISM: Eschericia coli

<400> SEQUENCE: 14

Leu Leu Val Ser Leu Asp Tyr Ser Gln Asn Glu Leu Arg
 1               5                  10

<210> SEQ ID NO 15
<211> LENGTH: 13
<212> TYPE: PRT
<213> ORGANISM: Eschericia coli

<400> SEQUENCE: 15

Val Leu Val Ala Leu Asp Tyr Ser Gln Asn Glu Leu Arg
 1               5                  10

<210> SEQ ID NO 16
<211> LENGTH: 13
<212> TYPE: PRT
<213> ORGANISM: Eschericia coli
```

-continued

<400> SEQUENCE: 16

Leu Leu Val Ala Leu Asp Tyr Ser Leu Lys Glu Leu Arg
1               5                   10

<210> SEQ ID NO 17
<211> LENGTH: 13
<212> TYPE: PRT
<213> ORGANISM: Eschericia coli

<400> SEQUENCE: 17

Leu Leu Val Ala Met Asp Tyr Ser Gln Gln Glu Leu Arg
1               5                   10

<210> SEQ ID NO 18
<211> LENGTH: 13
<212> TYPE: PRT
<213> ORGANISM: Eschericia coli

<400> SEQUENCE: 18

Leu Leu Val Ala Leu Asp Tyr Ser Leu Gln Glu Leu Arg
1               5                   10

<210> SEQ ID NO 19
<211> LENGTH: 13
<212> TYPE: PRT
<213> ORGANISM: Eschericia coli

<400> SEQUENCE: 19

Leu Val Val Ala Leu Asp Tyr Ser Gln Ile Asp Leu Arg
1               5                   10

<210> SEQ ID NO 20
<211> LENGTH: 13
<212> TYPE: PRT
<213> ORGANISM: Eschericia coli

<400> SEQUENCE: 20

Leu Leu Val Ala Leu Asp Tyr Ser Arg Ile Glu Phe Arg
1               5                   10

<210> SEQ ID NO 21
<211> LENGTH: 13
<212> TYPE: PRT
<213> ORGANISM: Eschericia coli

<400> SEQUENCE: 21

Leu Leu Val Ala Leu Asp Tyr Ser Gln Asn Glu Ile Arg
1               5                   10

<210> SEQ ID NO 22
<211> LENGTH: 13
<212> TYPE: PRT
<213> ORGANISM: Eschericia coli

<400> SEQUENCE: 22

Leu Leu Val Gly Leu Asp Tyr Ser Gln Ile Asp Leu Arg
1               5                   10

<210> SEQ ID NO 23
<211> LENGTH: 13
<212> TYPE: PRT
<213> ORGANISM: Eschericia coli

<400> SEQUENCE: 23

```
Leu Leu Val Val Leu Asp Tyr Ser Gln Ile Asp Leu Arg
 1               5                  10
```

<210> SEQ ID NO 24
<211> LENGTH: 13
<212> TYPE: PRT
<213> ORGANISM: Escericia coli

<400> SEQUENCE: 24

```
Leu Leu Val Asp Leu Asp Tyr Ser Gln Ile Asp Leu Arg
 1               5                  10
```

<210> SEQ ID NO 25
<211> LENGTH: 13
<212> TYPE: PRT
<213> ORGANISM: Eschericia coli

<400> SEQUENCE: 25

```
Leu Leu Val Asp Val Asp Tyr Ser Gln Ile Asp Leu Arg
 1               5                  10
```

<210> SEQ ID NO 26
<211> LENGTH: 13
<212> TYPE: PRT
<213> ORGANISM: Eschericia coli

<400> SEQUENCE: 26

```
Ile Leu Leu Ala Leu Asp Tyr Ser Gln Lys Glu Leu Arg
 1               5                  10
```

<210> SEQ ID NO 27
<211> LENGTH: 13
<212> TYPE: PRT
<213> ORGANISM: Eschericia coli

<400> SEQUENCE: 27

```
Leu Leu Met Ala Leu Asp Tyr Ser Gln Met Asp Leu Arg
 1               5                  10
```

<210> SEQ ID NO 28
<211> LENGTH: 13
<212> TYPE: PRT
<213> ORGANISM: Eschericia coli

<400> SEQUENCE: 28

```
Leu Leu Val Ala Leu Asp Phe Ser Gln Thr Asp Leu Arg
 1               5                  10
```

<210> SEQ ID NO 29
<211> LENGTH: 13
<212> TYPE: PRT
<213> ORGANISM: Eschericia coli

<400> SEQUENCE: 29

```
Leu Leu Val Val Val Asp Tyr Ser Gln Lys Glu Leu Arg
 1               5                  10
```

<210> SEQ ID NO 30
<211> LENGTH: 13
<212> TYPE: PRT
<213> ORGANISM: Eschericia coli

<400> SEQUENCE: 30

```
Leu Leu Val Ala Leu Asp Tyr Ser Gln Thr Glu Phe Trp
 1               5                  10
```

<210> SEQ ID NO 31
<211> LENGTH: 13
<212> TYPE: PRT
<213> ORGANISM: Eschericia coli

<400> SEQUENCE: 31

Leu Leu Val Ala Leu Asp Phe Ser Gln Thr Asp Leu Arg
 1               5                  10

<210> SEQ ID NO 32
<211> LENGTH: 13
<212> TYPE: PRT
<213> ORGANISM: Eschericia coli

<400> SEQUENCE: 32

Leu Leu Met Val Val Asp Tyr Ser Gln Ile Asp Leu Arg
 1               5                  10

<210> SEQ ID NO 33
<211> LENGTH: 13
<212> TYPE: PRT
<213> ORGANISM: Eschericia coli

<400> SEQUENCE: 33

Leu Leu Val Ala Leu Asp Tyr Arg Gln Lys Asp Leu Met
 1               5                  10

<210> SEQ ID NO 34
<211> LENGTH: 13
<212> TYPE: PRT
<213> ORGANISM: Eschericia coli

<400> SEQUENCE: 34

Arg Met Lys Ser Ile Asp Tyr Arg Gln Ile Glu Leu Arg
 1               5                  10

<210> SEQ ID NO 35
<211> LENGTH: 23
<212> TYPE: DNA
<213> ORGANISM: Eschericia coli

<400> SEQUENCE: 35
cgcgccgaat cccgctagc aat                                             23

<210> SEQ ID NO 36
<211> LENGTH: 43
<212> TYPE: DNA
<213> ORGANISM: Eschericia coli

<400> SEQUENCE: 36
cggaagcttg gctgcagaat attgctagcg ggaattcggc gcg                      43

<210> SEQ ID NO 37
<211> LENGTH: 49
YPE: DNA
RGANISM: Eschericia coli

<400> SEQUENCE: 37
cccgggaaat tccggaatt ccgattattg ctagcgggaa ttcggcgcg                 49

<210> SEQ ID NO 38
<211> LENGTH: 24
<212> TYPE: DNA

-continued

```
<213> ORGANISM: Eschericia coli

<400> SEQUENCE: 38
cgcgccgaat tcccgctagc aata                                              24

<210> SEQ ID NO 39
<211> LENGTH: 25
<212> TYPE: DNA
<213> ORGANISM: Eschericia coli

<400> SEQUENCE: 39
cgcgccgaat tcccgctagc aatat                                             25

<210> SEQ ID NO 40
<211> LENGTH: 26
<212> TYPE: DNA
<213> ORGANISM: Eschericia coli

<400> SEQUENCE: 40
cgcgccgaat tcccgctagc aatatc                                            26
```